(12) United States Patent
Dogaru

(10) Patent No.: US 6,822,443 B1
(45) Date of Patent: Nov. 23, 2004

(54) SENSORS AND PROBES FOR MAPPING ELECTROMAGNETIC FIELDS

(75) Inventor: Teodor Dogaru, Charlotte, NC (US)

(73) Assignee: Albany Instruments, Inc.

( * ) Notice: Subject to any disclaimer, the term of this patent is extended or adjusted under 35 U.S.C. 154(b) by 100 days.

(21) Appl. No.: 09/950,093

(22) Filed: Sep. 10, 2001

Related U.S. Application Data

(60) Provisional application No. 60/254,296, filed on Dec. 11, 2000, provisional application No. 60/247,245, filed on Nov. 13, 2000, and provisional application No. 60/231,752, filed on Sep. 11, 2000.

(51) Int. Cl.$^7$ .......................... G01N 27/82; G01R 33/09
(52) U.S. Cl. ........................................ 324/235; 324/238
(58) Field of Search ................................ 324/234, 235, 324/238, 239, 240, 242, 252, 268, 262; 338/32 R

(56) References Cited

U.S. PATENT DOCUMENTS

| | | | |
|---|---|---|---|
| 4,870,360 A | * | 9/1989 | Collins et al. .............. 324/235 |
| 5,019,777 A | | 5/1991 | Gulliver et al. |
| 5,450,009 A | * | 9/1995 | Murakami ............. 324/207.21 |
| 5,483,160 A | | 1/1996 | Gulliver et al. |
| 5,648,720 A | * | 7/1997 | Yarmchuk .................... 324/213 |
| 6,072,382 A | * | 6/2000 | Daughton et al. ........ 338/32 R |
| 6,150,809 A | | 11/2000 | Tiernan et al. |
| 6,504,363 B1 | * | 1/2003 | Dogaru et al. .............. 324/235 |

OTHER PUBLICATIONS

E.S. Boltz & T.C. Tieman, *New Electromagnetic Sensors for Detection of Substrate Cracking and Corrosion*, 17 Review of Progress in Quantitative Nondestructive Evaluation 1033–38 (1998).

E.S. Boltz et al., *Low–Frequency Magnetoresistive Eddy–Current Sensors for NDE of Aging Aircraft*, 3397 SPIE (1998).

* cited by examiner

*Primary Examiner*—N. Le
*Assistant Examiner*—Reena Aurora
(74) *Attorney, Agent, or Firm*—Lynn E. Barber

(57) ABSTRACT

Products are disclosed for measuring electromagnetic fields. One embodiment has at least two coplanar magneto-resestive sensors. Each magneto-resistive sensor has a sensitive axis in the plane of the at least two coplanar magneto-resistive sensors. The at least two magneto-resistive sensors may be orthogonally arranged about a central point to measure orthogonal components of electromagnetic fields.

36 Claims, 43 Drawing Sheets

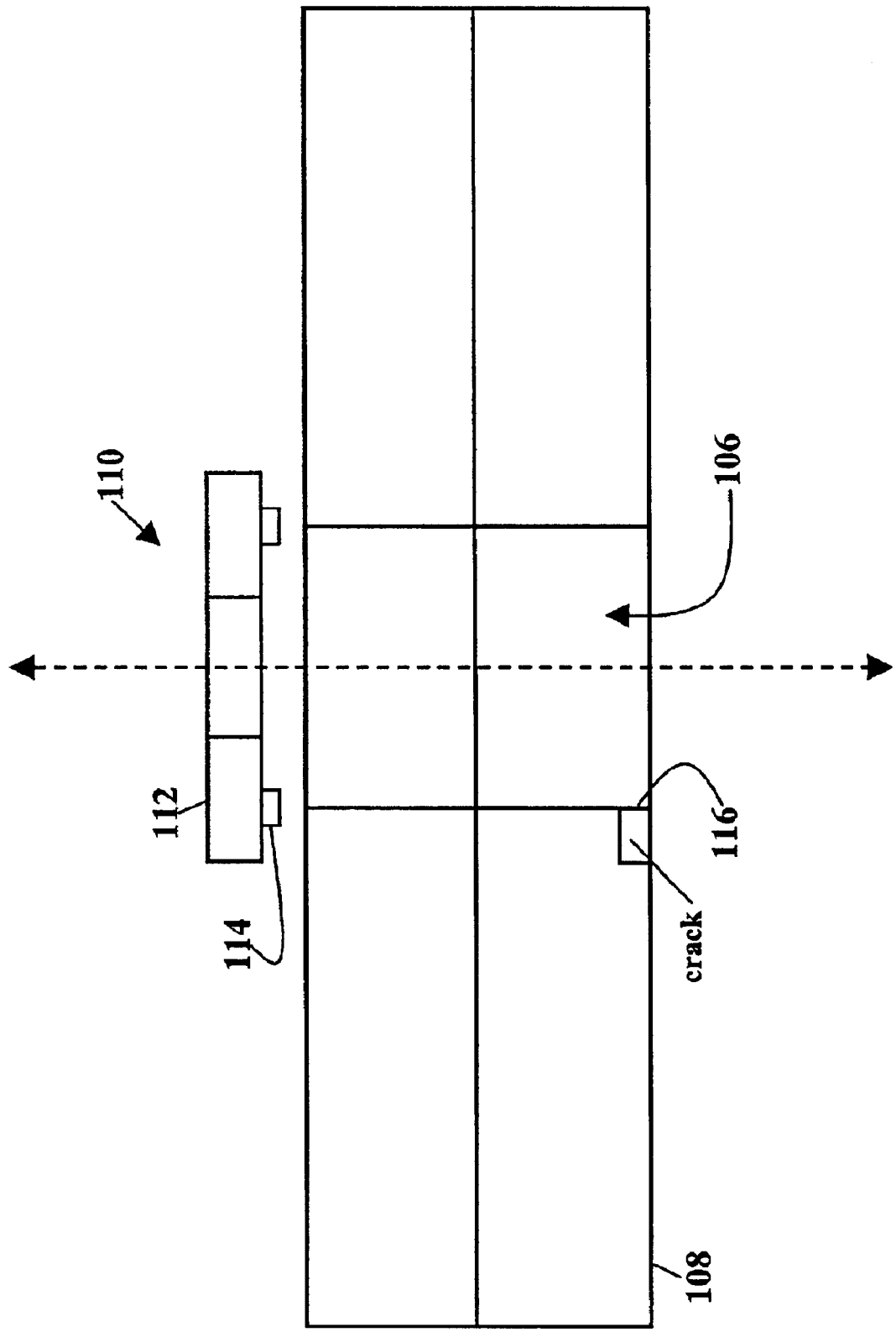

SENSORS AND PROBES FOR MAPPING ELECTROMAGNETIC FIELDS

CROSS-REFERENCE TO RELATED APPLICATIONS

This application claims the benefit of the following applications: U.S. Provisional Application No. 60/231,752, filed Sep. 11, 2000; U.S. Provisional Application No. 60/247,245, filed Nov. 13, 2000; and U.S. Provisional Application No. 60/254,296, filed Dec. 11, 2000.

NOTICE OF COPYRIGHT PROTECTION

A portion of the disclosure of this patent document and its figures contain material subject to copyright protection. The copyright owner has no objection to the facsimile reproduction by anyone of the patent document or the patent disclosure, but otherwise reserves all copyrights whatsoever.

BACKGROUND OF THE INVENTION

1. Field of the Invention

This invention generally relates to measuring and testing electricity and, more particularly, to sensors, to probes, and to arrays of probes and sensors for detecting and for mapping electromagnetic fields.

2. Description of the Related Art

The mapping of electromagnetic field vectors is extremely difficult and complex. "Mapping" refers to describing the magnitude and direction of electromagnetic field vectors. Once the components of an electromagnetic field vector are known, electromagnetic fields may be expressed at a location and time. Electromagnetic fields, however, are often extremely complex to mathematically describe. Analysis of the electromagnetic field vector may require differentiation, integration, gradient, and divergence operations of vector components over lines, surfaces, and three-dimensional volumes. This analysis is considerably complicated when the line, surface, or volume is complexly shaped and cannot be described using mathematics. Electromagnetic field mapping is also used to detect and diagnose flaws in electrically conductive materials, such as cracks, corrosion, holes, or material inhomogeneities. Therefore, experimental measuring of electromagnetic fields is essential to map those fields produced by sources of complex geometries that are difficult to describe theoretically, or to detect fields that can be produced by unknown sources.

In general, a magnetic sensor is used to experimentally measure electromagnetic fields. The sensor is placed within the electromagnetic field and measurements are taken. There are, however, several problems with existing electromagnetic sensors. Although the prior art sensors may be designed to measure electromagnetic fields in one dimension, the prior art sensors are still sensitive to electromagnetic field vector components in other dimensions. Another problem is frequency dependence of existing inductive sensors. Many existing inductive sensors only have an adequate output over a preferred frequency range. If the frequency of the electromagnetic field lies outside the preferred frequency range, the sensitivity of existing inductive sensors are greatly reduced and measurements are lost or compromised. Thus, although sensors are often used to measure complex electromagnetic fields, these problems with existing sensor designs still present limitations in the measurement of electromagnetic fields.

There is, accordingly, a need in the art for improved electromagnetic sensors which substantially isolate individual components of electromagnetic field vectors, electromagnetic sensors which are sensitive over a wide range of frequencies, electromagnetic sensors with a compact design, electromagnetic sensors which are cost effective to manufacture and to use, and electromagnetic sensors that can be manufactured in two-dimensional and three-dimensional arrays.

BRIEF SUMMARY OF THE INVENTION

The aforementioned problems are reduced by sensors of the present invention. A sensor according to the present invention is able to isolate individual vector components of electromagnetic fields. Sensors of the present invention measure two components of an electromagnetic field within a plane, essentially at the same point. Sensors of the present invention may also be arranged to measure three components of an electromagnetic field within a localized area about a central point. Because these sensors may have a small sensitive area, these sensors permit high-resolution electromagnetic field mapping. Sensors of the present invention may also be manufactured using planar technology, further permitting integrated sensor arrays for mapping fields without the need to scan test specimens. These sensors also allow the design of eddy current probes, and arrays of probes, for nondestructive testing and metallic profilometry, thus permitting new methods of detection of defects using these probes and arrays of probes.

One embodiment, for example, is substantially only sensitive in one direction. This embodiment has little to no response to electromagnetic fields in directions other than this single, sensitive direction. Sensors of the present invention, therefore, yield much more precise measurements of electromagnetic fields. Sensors of the present invention also exhibits a linear response and constant sensitivity over a wide range of frequencies, from DC to the megahertz domain. Because such sensors may be manufactured on silicon substrates, embodiments may be very small with high spatial resolution. Silicon substrate technology also allows many sensors to be manufactured on a single wafer. Sensors of the present invention are, therefore, small, precise, and inexpensive.

Another embodiment includes at least two coplanar magneto-resistive sensors. This embodiment measures two components of an electromagnetic field within a plane. Each magneto-resistive sensor measures the electromagnetic field along a sensitive axis in the plane of the at least two magneto-resistive sensors. The at least two magneto-resistive sensors may be orthogonally arranged to measure orthogonal components of the electromagnetic field in an area of intersection of the sensitive axes.

A further embodiment describes a product for measuring an electromagnetic field in two dimensions. This embodiment includes a first and a second magneto-resistive sensor. The first and second magneto-resistive sensors have a coplanar relationship and are arranged in a cruciform about a central point. The first magneto-resistive sensor has a first sensitive axis in the plane and measures the electromagnetic field along the first sensitive axis. The second magneto-resistive sensor has a second sensitive axis in the plane and measures the electromagnetic field along the second sensitive axis. The first and second magneto-resistive sensors measure orthogonal components of the electromagnetic field in an area of the central point.

Still another embodiment describes an electromagnetic product for measuring electromagnetic fields. The electromagnetic product has a plurality of devices, with each device comprising at least one pair of coplanar magneto-resistive sensors. Each magneto-resistive sensor has a sensitive axis in the plane and measures an electromagnetic field along the sensitive axis.

Another embodiment describes an electromagnetic product for measuring an electromagnetic field in three dimensions. This embodiment has at least two coplanar magneto-resistive sensors, with each magneto-resistive sensor having a sensitive axis in the plane of the at least two coplanar magneto-resistive sensors. A third sensor is sensitive to the electromagnetic field in a direction perpendicular to the at least two coplanar magneto-resistive sensors. The third sensor may utilize the Hall effect to measure the electromagnetic field.

Alternative embodiments describe a product for measuring electromagnetic fields. This product includes a plurality of devices arranged in a stack. Each device in the plurality of devices comprises at least one pair of coplanar magneto-resistive sensors, each magneto-resistive sensor having a sensitive axis in the plane of the device and measuring an electromagnetic field along the sensitive axis. The product measures the electromagnetic field at multiple locations within the stack. The plurality of devices may be arranged in a two-dimensional planar array, such as a sheet, or even a stack of two-dimensional planar arrays.

A further embodiment describes a product for mapping electromagnetic fields. This embodiment has at least two coplanar magneto-resistive sensors, each magneto-resistive sensor having a sensitive axis in the plane and measuring an electromagnetic field along the sensitive axis. The at least two magneto-resistive sensors are arranged about an area of intersection of the sensitive axes. A coil, carrying a current, biases each magneto-resistive sensor or compensates for background fields. The product maps magnitude and direction of the electromagnetic field in the plane. One or more magnets may also be used for biasing each magneto-resistive sensor.

Embodiments also include a product for detecting flaws in specimens. The product has a coil and at least two coplanar solid-state magnetic sensors and a third sensor. The coil induces an electromagnetic field in the specimen. The at least two coplanar solid-state magnetic sensors are arranged exterior to the coil, wherein the flaw creates a perturbation in the induced electromagnetic field, and the at least two solid-state magnetic sensors detect this perturbation to indicate the flaw. The at least two solid-state magnetic sensors may include giant magneto-resistive (GMR) sensors, spin-dependent tunneling (SDT) sensors, anisotropic magneto-resistive (AMR) sensors, and Hall effect sensors. The coil may have a cylindrical configuration surrounding the two coplanar solid-state magnetic sensors. The coil could also have a flat configuration, placed exterior to the sensor, and optionally centered about a central point. A probe that utilizes a one-directional spin-dependent tunneling (SDT) sensor, for example, could comprise a flat coil placed exterior to the sensor and centered about the sensor.

Still a further embodiment describes a product for mapping flaws in specimens. A coil induces an electromagnetic field in a specimen. At least two coplanar magneto-resistive sensors each measure the induced electromagnetic field along a sensitive axis in the plane. The at least two magneto-resistive sensors are arranged to measure the induced electromagnetic field in an area of intersection of the sensitive axes, wherein a flaw creates a perturbation in the induced electromagnetic field, and the at least two magneto-resistive sensors detect this perturbation to map the flaw. The area of intersection typically includes the active area of each sensor.

Still another embodiment discloses a product for mapping flaws in specimens. A coil induces an electromagnetic field in the specimen. A first magneto-resistive sensor and a second magneto-resistive sensor have a coplanar relationship and are orthogonally arranged. The first magneto-resistive sensor measures the induced electromagnetic field along a first sensitive axis in the plane. The second magneto-resistive sensor measures the induced electromagnetic field along a second sensitive axis in the plane. The first and second magneto-resistive sensors measure orthogonal components of the induced electromagnetic field in an area of the central point. A perpendicular sensor measures perturbations in the induced electromagnetic field in a direction perpendicular to the plane of the at least two coplanar magneto-resistive sensors. The flaw creates a perturbation in the induced electromagnetic field, and the orthogonal arrangement of the first and second magneto-resistive sensors detects orthogonal components of this perturbation, and the orthogonal components map the flaw. The product, having the first and the second magneto-resistive sensors, enables the mapping of a randomly-oriented crack or determining the orientation of a crack having an unknown orientation.

BRIEF DESCRIPTION OF THE DRAWINGS

These and other features, aspects, and advantages of the present invention are better understood when the following Detailed Description of the Invention is read with reference to the accompanying drawings, wherein:

FIGS. 24 and 25 are sectional views of probes demonstrating the use of a circular array of sensors;

DETAILED DESCRIPTION OF THE INVENTION

Figure 1:
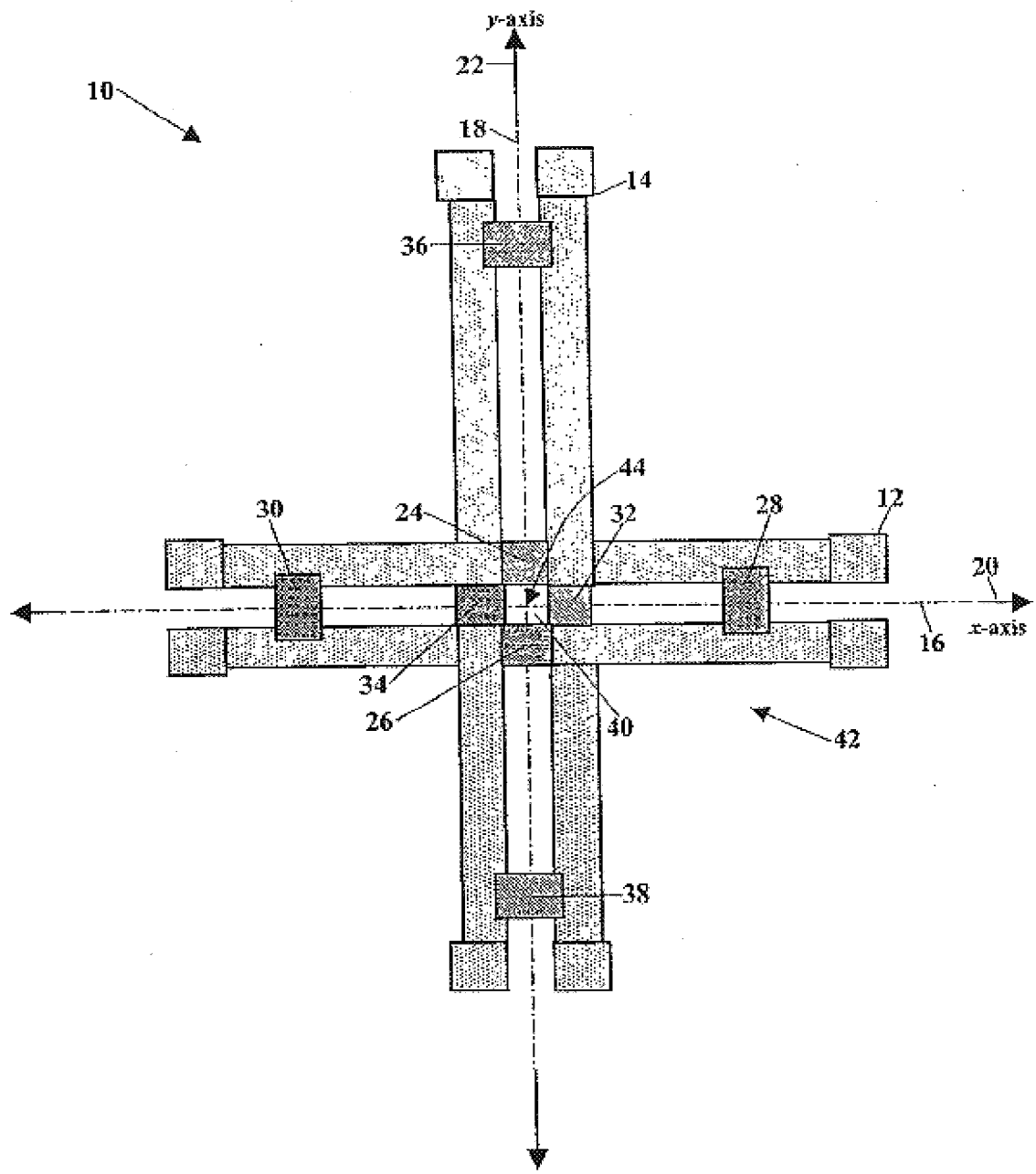
FIG. 1 is a schematic drawing showing a two-directional GMR sensor for measuring electromagnetic fields within its plane.

The present invention utilizes two-dimensional and three-dimensional configurations of electromagnetic sensors. The sensors herein described isolate individual vector components of electromagnetic fields. A two-dimensional sensor of the present invention measures two components of an electromagnetic field within a plane. A three-dimensional sensor, on the other hand, measures three components of an electromagnetic field within a localized area. For those readers unfamiliar with the general concept and use of two-dimensional and of three-dimensional sensors, the following references, all of which are incorporated herein by reference in their entirety, may be consulted: L. Chiesi et al., *CMOS Planar 2D Micro-Fluxgate Sensor*, 82 SENSORS AND ACTUATORS A: PHYSICAL 174-80 (2000); C. Schott et al., *Single-Chip 3-D Silicon Hall Sensor*, 82 SENSORS AND ACTUATORS A: PHYSICAL 167-73 (2000); and F. Burger et al., *New Fully Integrated 3-D Silicon Hall Sensor for Precise Angular-Position Measurements*, 67 SENSORS AND ACTUATORS A: PHYSICAL 72-76 (1998).

The sensors described herein may utilize any of the following sensor technologies: giant magneto-resistive (GMR) sensors, geometric magneto-resistance sensors, spin-dependent tunneling (SDT) sensors, anisotropic magneto-resistive (AMR) sensors, and Hall effect sensors. While those of ordinary skill in the art may be familiar with these sensor technologies, those unfamiliar with sensor technologies may consult the following references, all of which are incorporated herein by reference in their entirety: J. Daughton et al., *Magnetic Field Sensors Using GMR Multilayer*, 30 IEEE TRANSACTIONS ON MAGNETICS 4608-10 (1996); M. Tondra et al., *Micromagnetic Design of Spin-Dependent Tunnel Junctions for Optimized Sensor Performance*, J. APPLIED PHYSICS [awaiting publication—will amend with citation]; U.S. Pat. No. 6,072,071 issued to Daughton et al. (Jun. 6, 2000); U.S. Pat. No. 5,617,071 issued to Daughton (Apr. 1, 1997); U.S. Pat. No. 5,595,830 issued to Daughton (Jan. 21, 1997); U.S. Pat. No. 5,569,544 issued to Daughton (Oct. 29, 1996); and S. A. Solin et al., *Enhanced Room-Temperature Geometric Magnetoresistance in Inhomogenous Narrow-Gap Semiconductors*, 289 SCIENCE 1530-32 (2000).

Those of ordinary skill in the art may also have read the inventors' published research reports, all of which are incorporated herein by reference in their entirety: Teodor Dogaru et al., *New Directions in Eddy Current Sensing Technology*, SENSORS MAGAZINE, June 2000, at 56–62; Teodor Dogaru et al., *A GMR-Based Eddy-Current Sensor*, 37 IEEE TRANSACTIONS ON MAGNETICS, No. 5 (September 2000); Teodor Dogaru et al., *Detection of Cracks Near Sharp Edges Using a GMR Eddy Current Sensor*, in SPIE PROCEEDINGS—NONDESTRUCTIVE EVALUATION OF AGING AIRCRAFT, AIRPORTS, AND AEROSPACE HARDWARE IV 2111-16 (Ajit K. Mal ed., 2000); Teodor Dogaru et al., *Integrated Giant Magnetoresistive Transducer for Eddy Current Testing*, in PROCEEDINGS—15$^{Th}$ WORLD CONFERENCE ON NON-DESTRUCTIVE TESTING (Oct. 15–21, 2000) <http://www.ndt.net/article/wcndt00/papers/idn565/idn565.htm>; Smith S. T. et al., *A Giant Magnetoresistive Eddy Current Sensor for Use as a Zero-Width Coordinate Measuring Machine Probe*, in 22 PROCEEDINGS—AMERICAN SOCIETY OF PRECISION ENGINEERING 533-36 (2000); and Smith C. S. et al., *Non-Destructive Test Utilizing Spin Dependent Tunneling Sensors*, [MAT2001 Conference awaiting publication—will amend with citation]. Although the references cited in the above three paragraphs may be helpful to the reader, the applicants do not represent that the material therein is prior art to the present application.

FIG. 1 is a schematic drawing showing a two-directional GMR sensor 10 for measuring electromagnetic fields within its plane. The sensor 10 utilizes giant magneto-resistive sensors that vary in electrical resistance when exposed to a magnetic field. The sensor 10 includes a first magneto-resistive sensor 12 and a second magneto-resistive sensor 14. The first magneto-resistive sensor 12 detects an electromagnetic field along a corresponding first sensitive axis 16. The second magneto-resistive sensor 14, likewise, detects the electromagnetic field along a corresponding second sensitive axis 18. The first magneto-resistive sensor 12 and the second magneto-resistive sensor 14 each have very little response to components of the electromagnetic field in any direction not along their respective sensitive axes 16 and 18.

The sensor 10 measures planar components of electromagnetic fields. The first magneto-resistive sensor 12 and the second magneto-resistive sensor 14 have a coplanar arrangement. Because first sensitive axis 16 and the second sensitive axis 18 lie within the same plane, the sensor 10 is only sensitive to components of electromagnetic fields within the plane. FIG. 1 shows the first magneto-resistive sensor 12 orthogonally arranged to the second magneto-resistive sensor 14. The first magneto-resistive sensor 12 is shown aligned with an x-axis 20, while the second magneto-resistive sensor 18 is aligned with a y-axis 22. Because the first sensitive axis 16 is, likewise, orthogonally arranged to the second sensitive axis 18, the first and second magneto-resistive sensors 12 and 14 detect orthogonal components of electromagnetic fields.

FIG. 1 also shows that the sensor 10 measures electromagnetic fields about a small area The first magneto-resistive sensor 12 includes a pair of variable resistors 24 and 26 in a bridge configuration, on opposing arms of the bridge, with a pair of electromagnetically-shielded balance resistors 28 and 30. The second magneto-resistive sensor 14, likewise, includes opposing, variable resistors 32 and 34 in a bridge configuration with electromagnetically-shielded balance resistors 36 and 38. The variable resistors 24 and 26 sense components of the electromagnetic field along the first sensitive axis 16. The variable resistors 32 and 34 sense components of the electromagnetic field along the second sensitive axis 18. The variable resistors 24, 26, 32, and 34 are arranged about an area of intersection 40 of the first sensitive axis 16 and the second sensitive axis 18. The variable resistors 24, 26, 32, and 34 thus define the area of intersection 40 and, correspondingly, the area sensitive to electromagnetic fields. Because the variable resistors 24, 26, 32, and 34 each have dimensions of about twenty five micrometers (25 μm) by fifty micrometers (50 μm), the size of the area of intersection 40 is about one hundred micrometers by about one hundred micrometers (100 μm×100 μm). The size of the area of intersection 40, and thus the size of the area sensitive to electromagnetic fields, is substantially smaller than previous sensor designs.

The small size of the area of intersection 40 permits localized electromagnetic field measurements. Because the first 12 and second 14 magneto-resistive sensors have a coplanar relationship and are arranged in a cruciform 42 about the area of intersection 40, the first 12 and second 14 magneto-resistive sensors measure orthogonal components of the electromagnetic field about the small area of intersection 40. For many applications this small area of intersection 40, again about one hundred micrometers by about one hundred micrometers (100 μm×100 μm), represents measuring orthogonal components of an electromagnetic field at essentially a single, central point 44. Such a small sensitive area 40 is especially useful when experimental mapping of electromagnetic fields provides the most reliable analysis tool.

The sensor 10 is used to locally detect the magnitude and direction of an externally-applied electromagnetic field within the plane of the sensor 10. Because the sensor 10 only detects components of magnetic fields in the plane of the sensor 10, the magnitude of the in-plane magnetic field may be calculated from $$|B| = \sqrt{B_x^2 + B_y^2}$$

and the first-quadrant orientation of the magnetic field is $$\phi = \tan^{-1}\frac{B_y}{B_x}.$$

Figure 2:
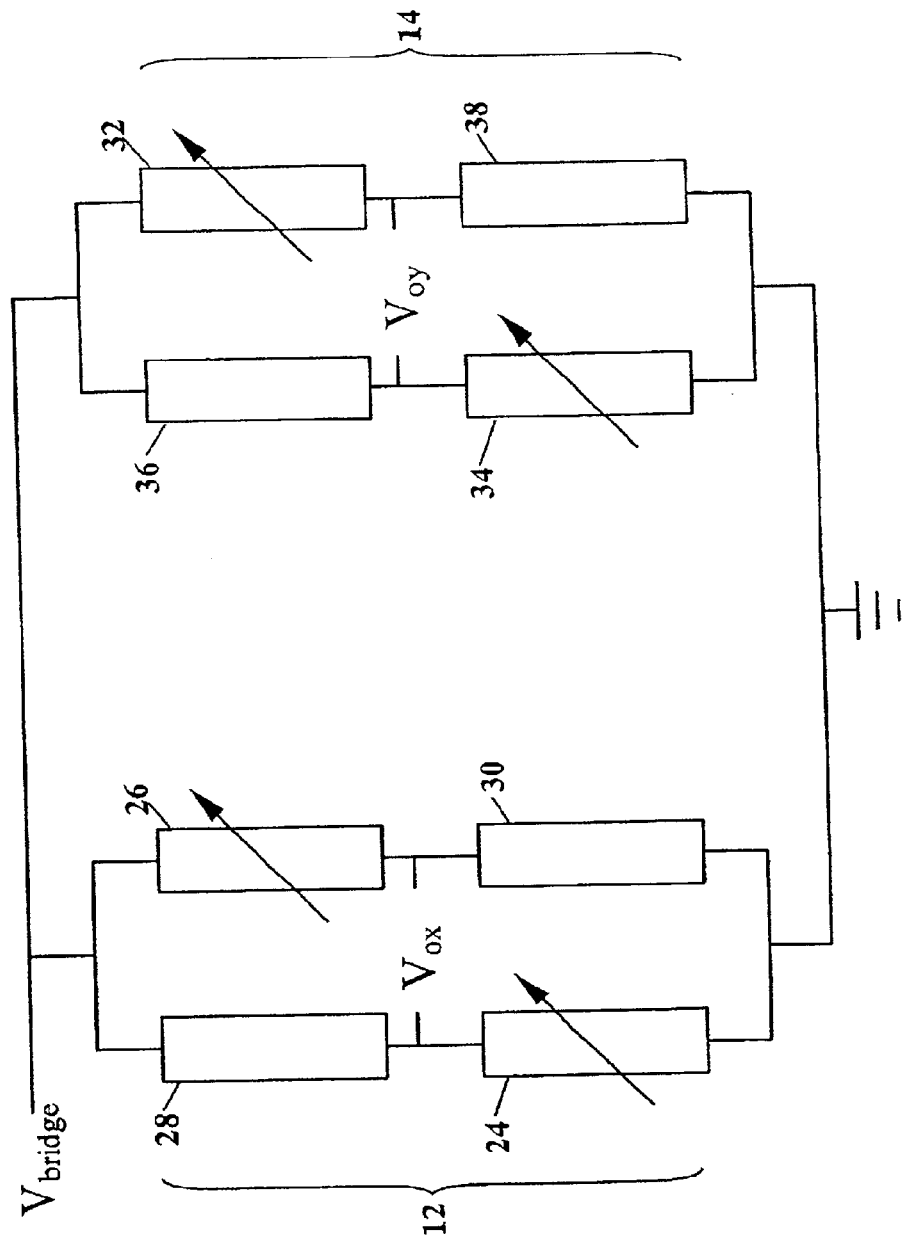
FIG. 2 is an equivalent electrical schematic drawing of the sensor shown in FIG. 1.

FIG. 2 is an equivalent electrical schematic drawing of the sensor 10 shown in FIG. 1. FIG. 2 shows the bridge arrangement of each magneto-resistive sensor. The first magneto-resistive sensor 12 includes the opposing, variable resistors 24 and 26, and the electromagnetically-shielded balance resistors 28 and 30, in a bridge configuration. The second magneto-resistive sensor 14, likewise, includes the opposing, variable resistors 32 and 34 in a bridge configuration with the electromagnetically-shielded balance resistors 36 and 38. The two orthogonal bridge configurations are connected to the same power supply $V_{bridge}$. The two orthogonal bridge configurations may also use separate power supplies, so that the voltage across each bridge configuration may be independently adjusted.

Figure 3:
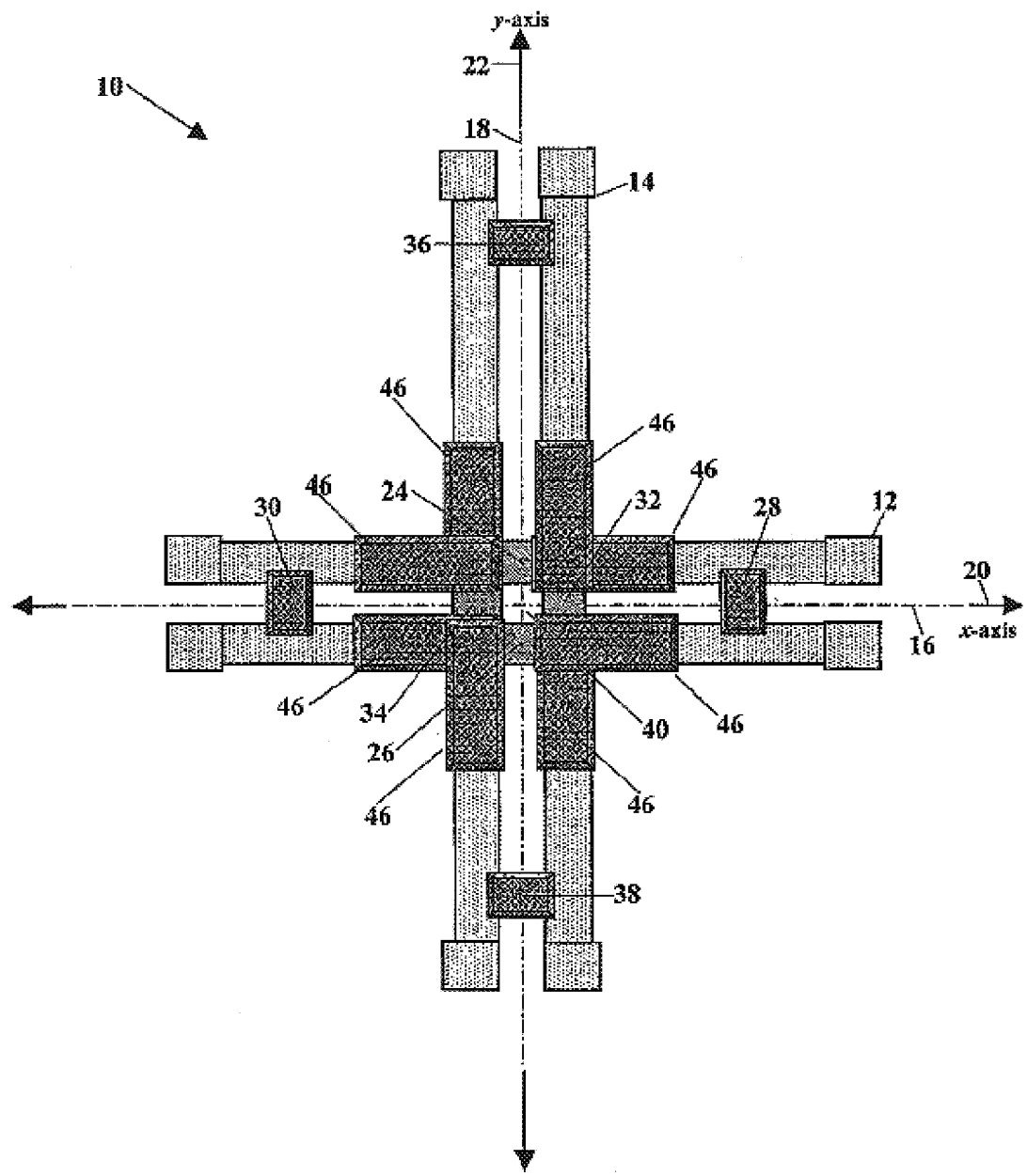
FIGS. 3–5 are schematic drawings showing alternative embodiments of the sensor for measuring electromagnetic fields.

FIG. 3 is a schematic drawing showing an alternative embodiment of the sensor 10 for measuring electromagnetic fields. FIG. 3 shows the sensor 10 may also include one or more flux concentrators 46 to enhance sensitivity. A magnetic flux concentration factor is dependent upon the ratio between the length of the each flux concentrator and the gap between the opposing, variable resistors 24, 26 and 32, 34. While the added flux concentrators 46 increase the overall size of the sensor 10, the enhanced sensitivity may offset the drawback of a larger sensor die area.

Figure 4:
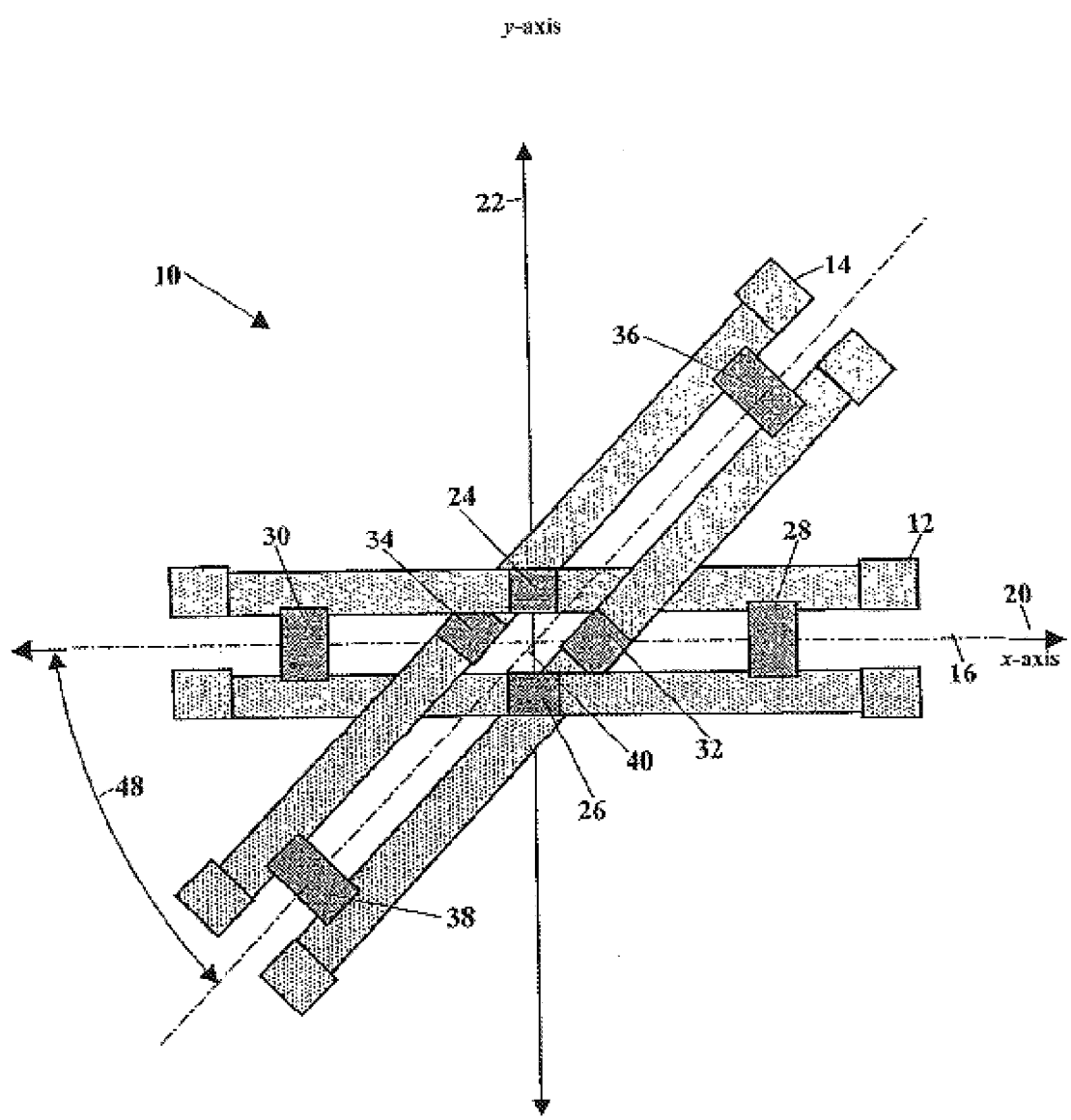
Figure 5:
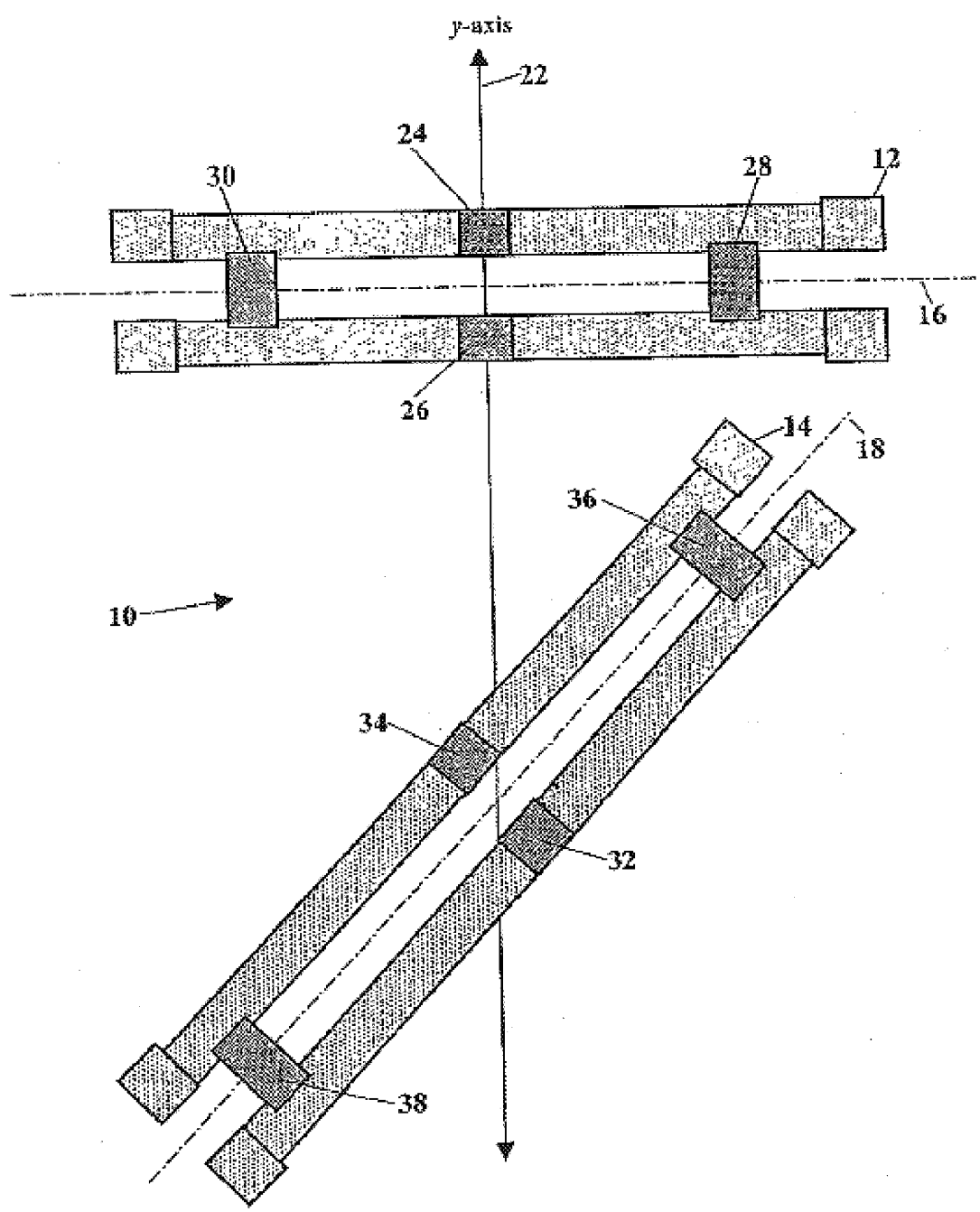

FIGS. 4 and 5 are schematic drawings showing alternative embodiments of a sensor for measuring electromagnetic fields. While FIG. 1 shows the first magneto-resistive sensor 12 orthogonally arranged to the second magneto-resistive sensor 14, FIG. 4 shows an acute angle arrangement 48. The first sensitive axis 16 and the second sensitive axis 18 lie within the same plane, and the sensor 10 measures components of electromagnetic fields within the area of intersection 40. The sensor 10 shown in FIG. 4, however, allows mapping of diverse components of electromagnetic fields. The sensor 10 may be designed and formed with any acute angle arrangement 48. The ability to design and form custom-oriented acute angle arrangements allows engineers and scientists to map complex electromagnetic fields and geometries. FIG. 5 shows the first magneto-resistive sensor 12 and the second magneto-resistive sensor 14 oriented to measure electromagnetic fields in differing locations.

Figure 6:
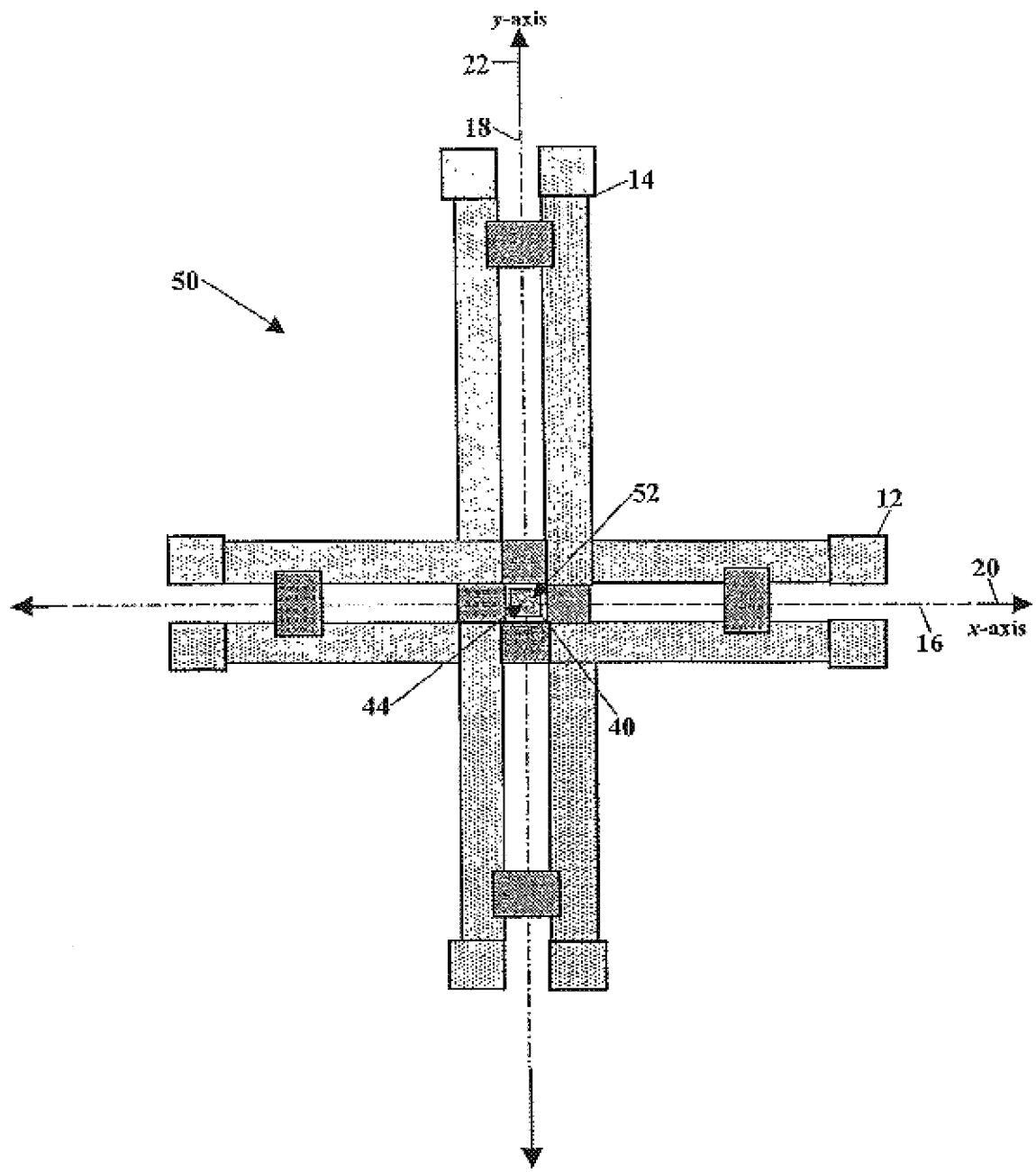
FIG. 6 is a schematic drawing showing a sensor for measuring an electromagnetic field in three dimensions.

FIG. 6 is a schematic drawing showing a sensor 50 for measuring an electromagnetic field in three dimensions. This sensor 50 includes the first magneto-resistive sensor 12 and the coplanar second magneto-resistive sensor 14. The first magneto-resistive sensor 12 detects an electromagnetic field along the first sensitive axis 16. The second magneto-resistive sensor 14, likewise, detects the electromagnetic field along the second sensitive axis 18. The first sensitive axis 16 and the second sensitive axis 18 are arranged such that the area of intersection 40 is also the area sensitive to electromagnetic fields. A third sensor 52 also measures the electromagnetic field in the area of intersection 40, but the third sensor 52 measures a component perpendicular to the plane of the sensor 50. The first magneto-resistive sensor 12, the coplanar second magneto-resistive sensor 14, and the third sensor 52 combine to measure electromagnetic fields in three dimensions. If the first magneto-resistive sensor 12 and the second magneto-resistive sensor 14 are orthogonally arranged, as shown in FIG. 6, then the sensor 50 measures three orthogonal components of the electromagnetic field. The first magneto-resistive sensor 12, and the coplanar second magneto-resistive sensor 14 could comprise any of giant magneto-resistive (GMR) sensors, spin-dependent tunneling (SDT) sensors, anisotropic magneto-resistive (AMR) sensors, and Hall effect sensors.

The third sensor 52 is preferably a Hall effect sensor. The Hall effect sensor 52 may be formed on the same substrate as the first magneto-resistive sensor 12 and the second magneto-resistive sensor 14. While the first magneto-resistive sensor 12 and the second magneto-resistive sensor 14 are sensitive in the area of intersection 40, the Hall effect sensor 52 is only sensitive about a distance of a few microns perpendicular to the plane of the sensor 50. This sensitivity in a z-axis generally reflects the depth of the buried layer of the horizontal Hall effect sensor 52. This limited sensitivity further represents measuring orthogonal components of an electromagnetic field at essentially the single, central point 44. As those of ordinary skill understand, a magnetic field B produces a transverse electric field E in the conducting third sensor 52, and the third sensor 52 detects the voltage across the conducting material. See DAVID K. CHENG, FIELD AND WAVE ELECTROMAGNETICS 282-283 (1989), incorporated herein by reference, for a description of the Hall effect.

Figure 7:
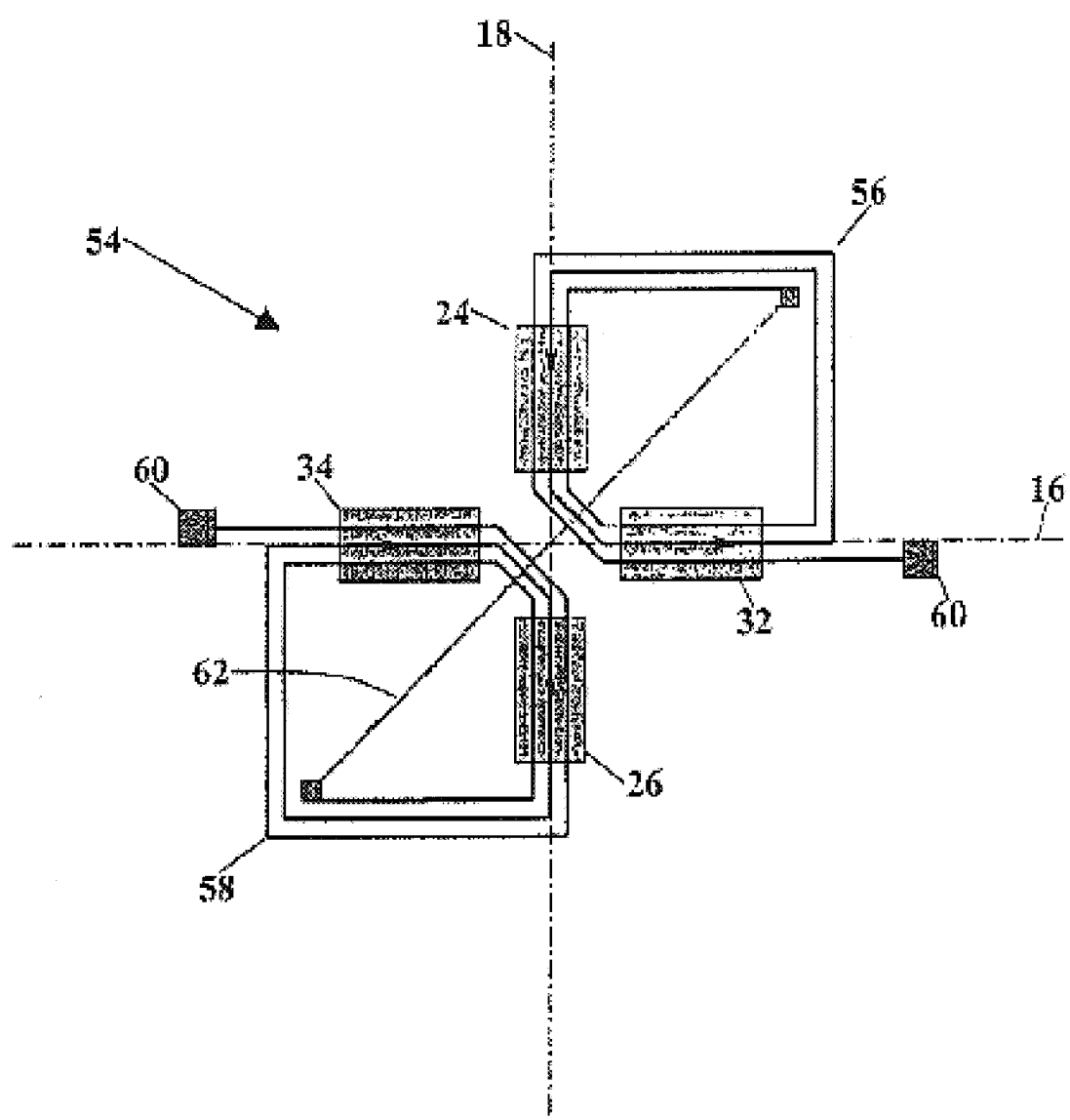
FIG. 7 is a schematic drawing of a two-directional GMR bipolar sensor incorporating an integrated coil.

FIG. 7 is a schematic drawing of a two-directional GMR bipolar sensor 54 incorporating an integrated coil. The sensor 54 is made bipolar by applying a DC bias field along the sensitive axis of each magneto-resistive sensor. As FIG. 7 shows, built-on integrated coils 56 and 58 produce a DC bias field along the first sensitive axis 16 and along the second sensitive axis 18. The bipolar sensor 54 may thus detect both the magnitude and the direction of an applied magnetic field in the plane of the sensor 54. Substrate pads 60, and via 62, complete the circuit. The embodiment shown in FIG. 7 represents only one possible biasing configuration. Those of ordinary skill in the art now recognize that variations of the configuration shown in FIG. 7 are within the scope of the present invention. One variation, for example, could include an external magnet oriented at forty-five degrees (45°) to the sensitive axes.

Figure 8:
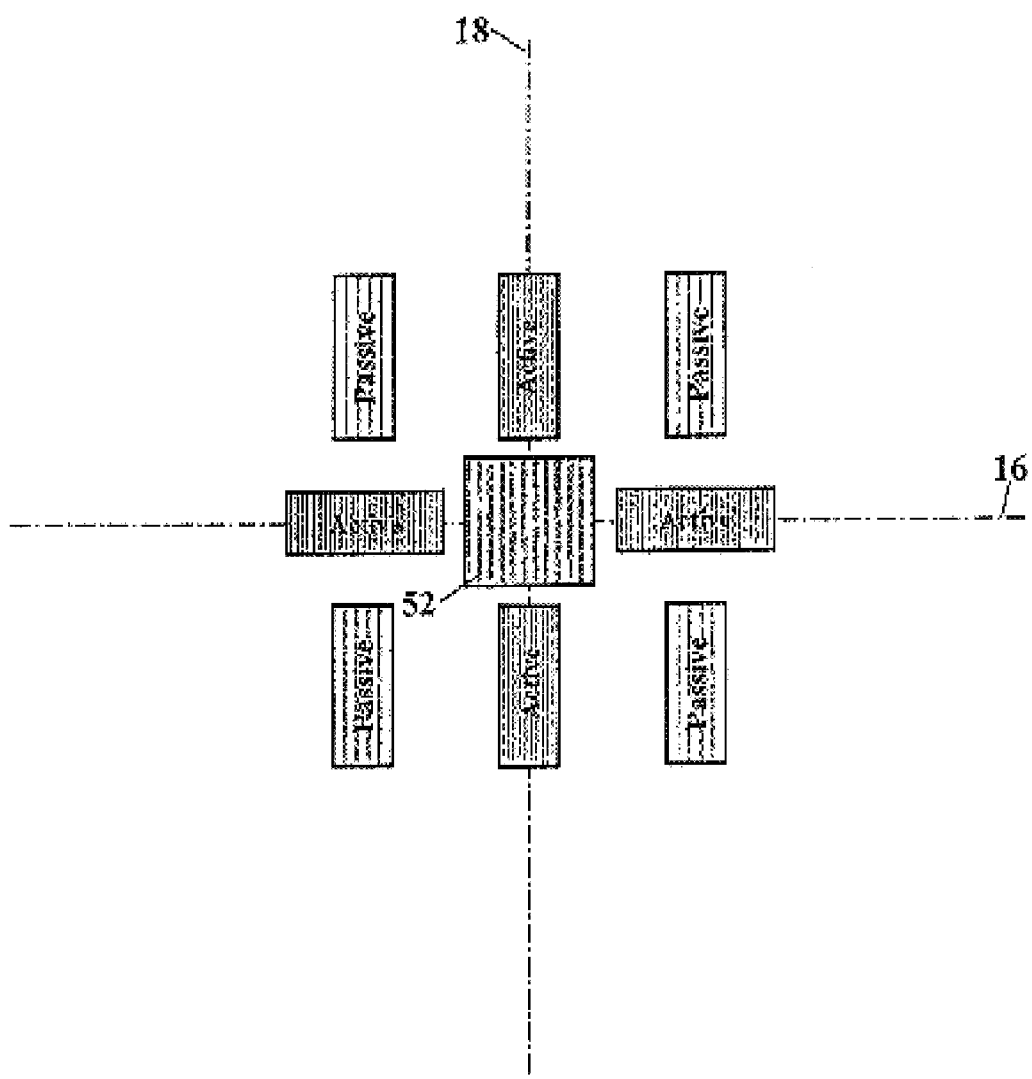
FIG. 8 is a schematic drawing of a compact hybrid GMR three-directional sensor.

FIG. 8 is a schematic drawing of a compact hybrid GMR three-directional sensor. This compact hybrid GMR three-directional sensor includes the third sensor 52 to measure perpendicular components. This design does not include flux concentrators, therefore, the sensitive area is reduced to allow high spatial resolution electromagnetic field mapping. In general magneto-resistive sensors have higher sensitivity than Hall effect sensors, therefore, in some applications, it might be desirable to bring both types of sensors in the same range of sensitivity. Magneto-resistive sensors, whether giant magneto-resistive (GMR) sensors, spin-dependent tunneling (SDT) sensors, or anisotropic magneto-resistive (AMR) sensors, could saturate above a certain field level. If there is a large saturation difference between the magneto-resistive sensors and the Hall effect sensors, the magneto-resistive sensors may saturate at such low fields that the Hall effect sensors may not discriminate. Below are some techniques for equalizing the sensitivity ranges of the magneto-resistive sensors and the Hall effect sensors:

1. As FIG. 8 shows, the magneto-resistive sensors do not contain flux concentrators (shown as reference numeral 46 in FIG. 3). Eliminating flux concentrators reduces the sensitivity of the magneto-resistive sensors, and increases the saturation field, by about a factor of ten (10). Eliminating the flux concentrators also reduces the size of the sensor package, thus increasing the density of manufactured sensor arrays.

2. Apply a high current to the Hall effect third sensor (shown as reference numeral 52 in FIG. 6). Thermal heating limits current density flowing through the Hall effect device.

The Hall effect sensor (shown as reference numeral 52 in FIG. 8) is first manufactured, requiring masks for diffusion of the device area and for diffusion of the current and voltage contacts. The area occupied by the Hall effect third sensor is approximately fifty micrometers by fifty micrometers (50 $\mu$m×50 $\mu$m). After these first diffusions are completed, magneto-resistive films are applied for patterning. The magneto-resistive sensor elements are not overlapped on the Hall effect third sensor, so the performance of the magneto-resistive sensors are little affected by the Hall effect third sensor processing steps. The performance of the Hall effect third sensor, likewise, is little affected by the magneto-resistive sensor processing steps.

Figure 9:
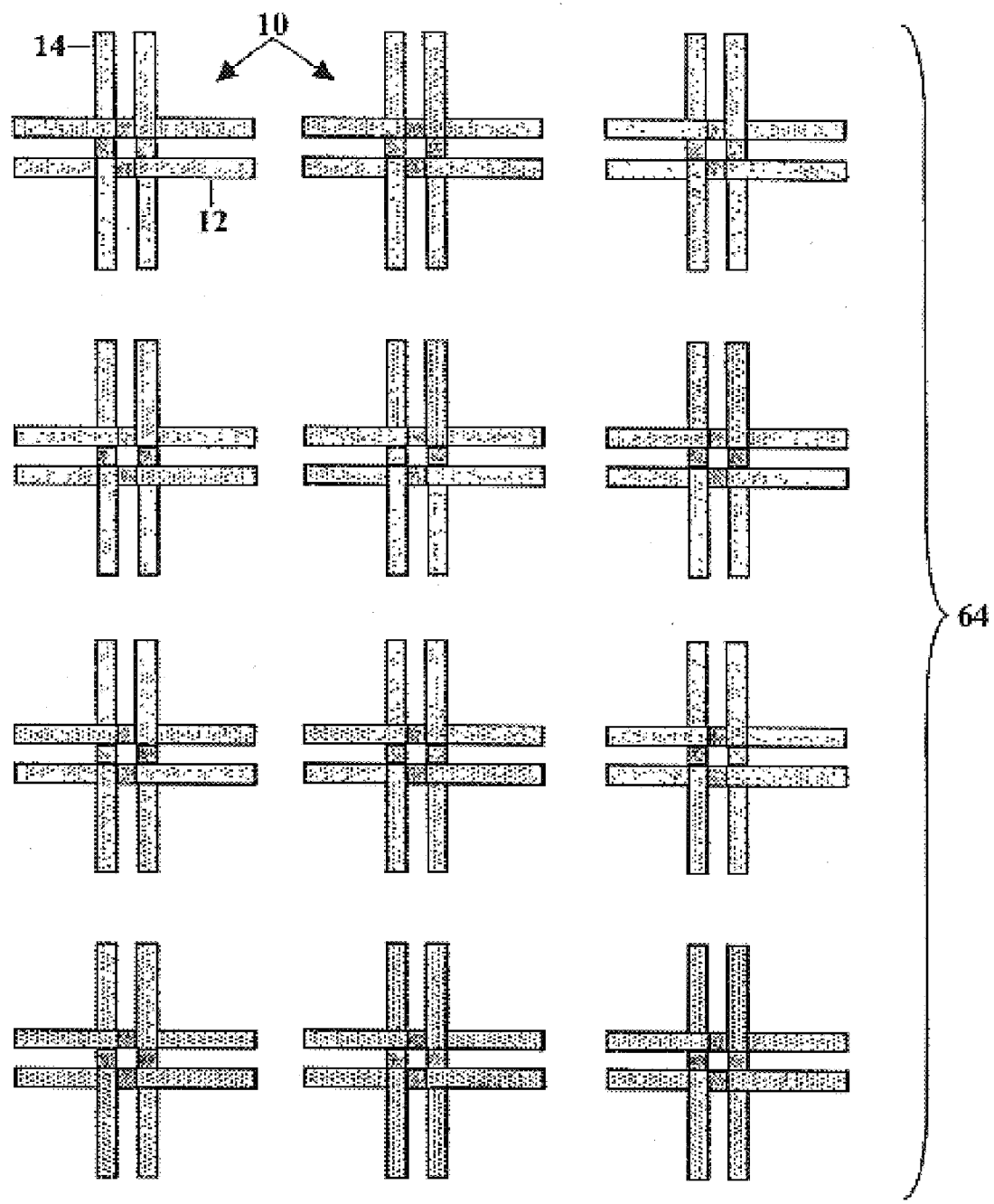
FIGS. 9 and 10 are schematic drawings of sensor arrays.
Figure 10:
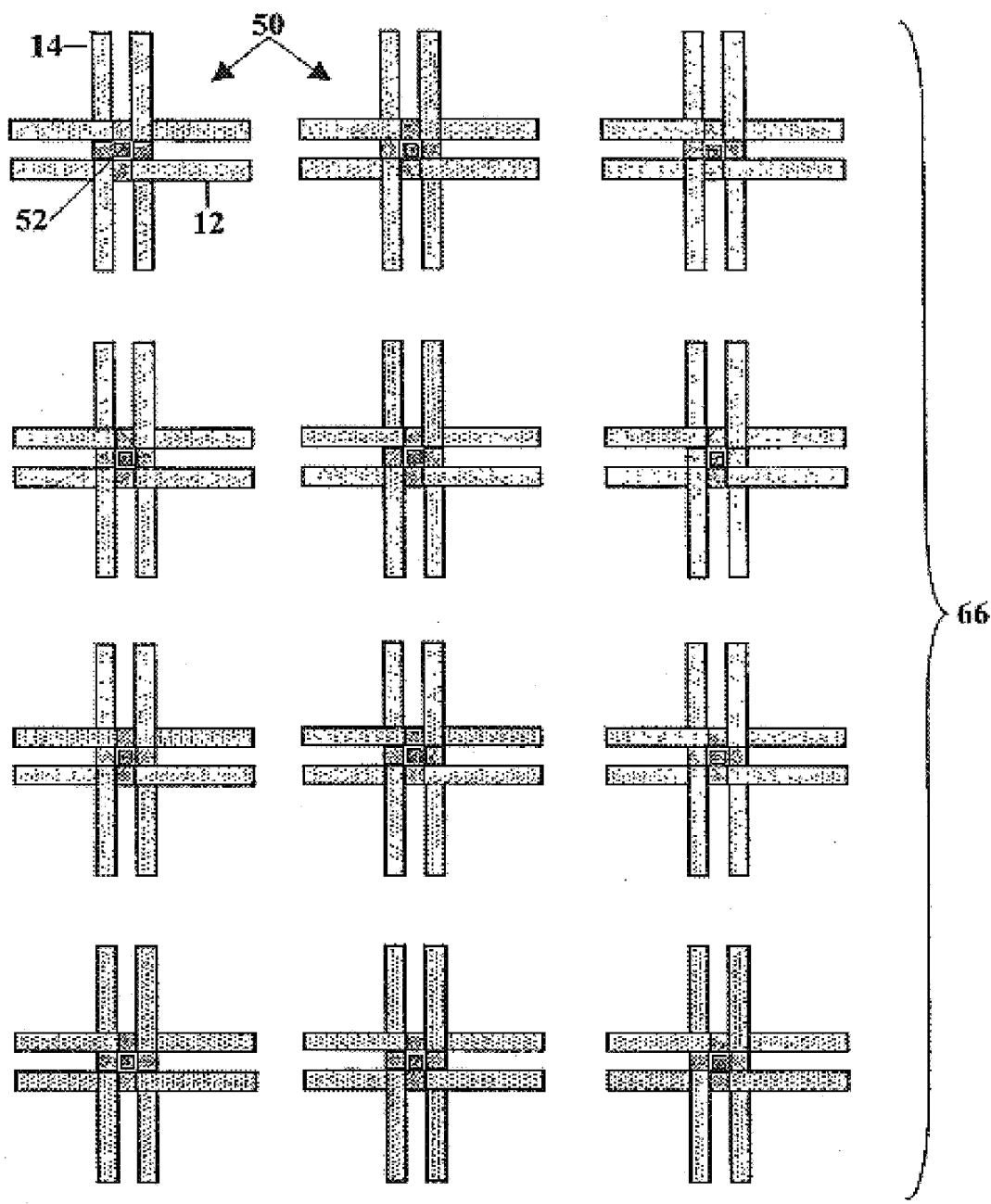

FIGS. 9 and 10 are schematic drawings of sensor arrays. FIG. 9 shows a two-dimensional array 64 comprising a plurality of the orthogonally-arranged sensor 10 shown in FIG. 1. The array 64 is uniformly disposed to map electromagnetic fields in the plane of the array 64. FIG. 10, likewise, shows a sensor array 66 comprising a plurality of the three-dimensional sensor 50 shown in FIG. 6. The array 68 is also uniformly disposed to map electromagnetic fields in the plane of the array 68. The sensors 10 and/or 50 may be integrated on a silicon chip substrate using planar technology. If, for example, the first magneto-resistive sensor 12 and the second magneto-resistive sensor 14 are orthogonally arranged, the in-plane components and the in-plane vector of an electromagnetic field, at many various locations, could be determined. Each individual sensor 10 and/or 50 could be positioned where desired to map a specific geometry of magnetic field. The sensor arrays 64 and 66 could also be designed to map printed circuit boards for magnetic flux intensity, magnetic flux density, and other instances of electromagnetic induction. Those of ordinary skill now understand the sensor arrays 64 and 66 may comprise any of the sensors shown in FIGS. 1–8. Those of ordinary skill also now understand the sensor arrays 64 and 66 may comprise any combination of the sensors shown in FIGS. 1–8. The sensor arrays 64 and 66 may also be used to map the electromagnetic field created by coils or magnets of different geometries, to detect and map unknown electromagnetic fields in a region of space, or to map defects or discontinuities in conductive materials. The sensor arrays 64 and 66 may also be used to map metallic profiles, to image the granular structure of metallic alloys, such as titanium alloys, and to map the magnetic domain structure in ferromagnetic materials. The sensor arrays 64 and 66, therefore, exhibit increased sensitivity and increased spatial resolution. The sensor arrays 64 and 66 are also more cost effective because of planar integration on silicon. The sensor arrays 64 and 66 also eliminate scanning, thus resulting in more rapid imaging and reduced costs.

Figure 11:
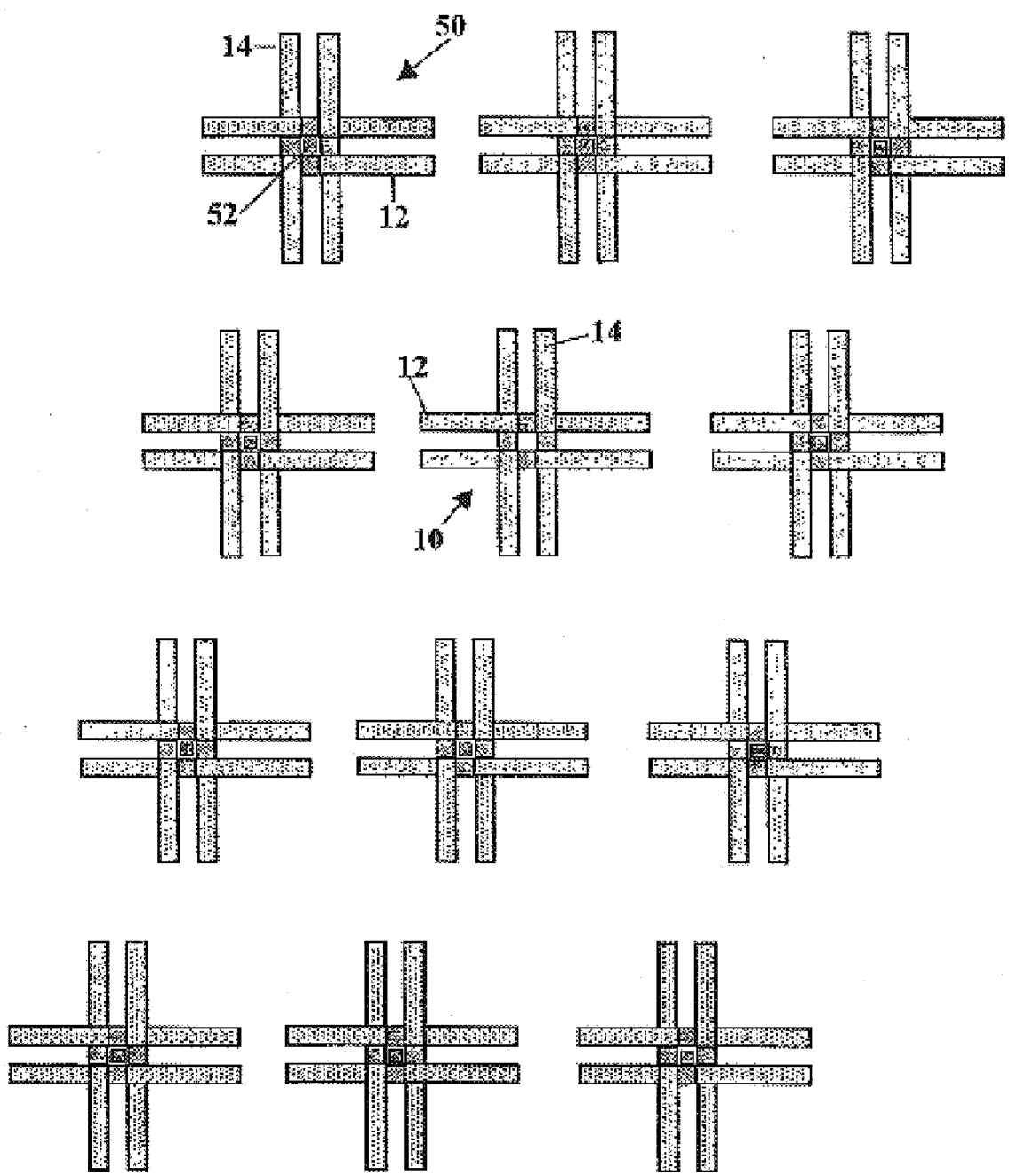
FIGS. 11 and 12 are schematic drawings of arrays of other configurations.
Figure 12:
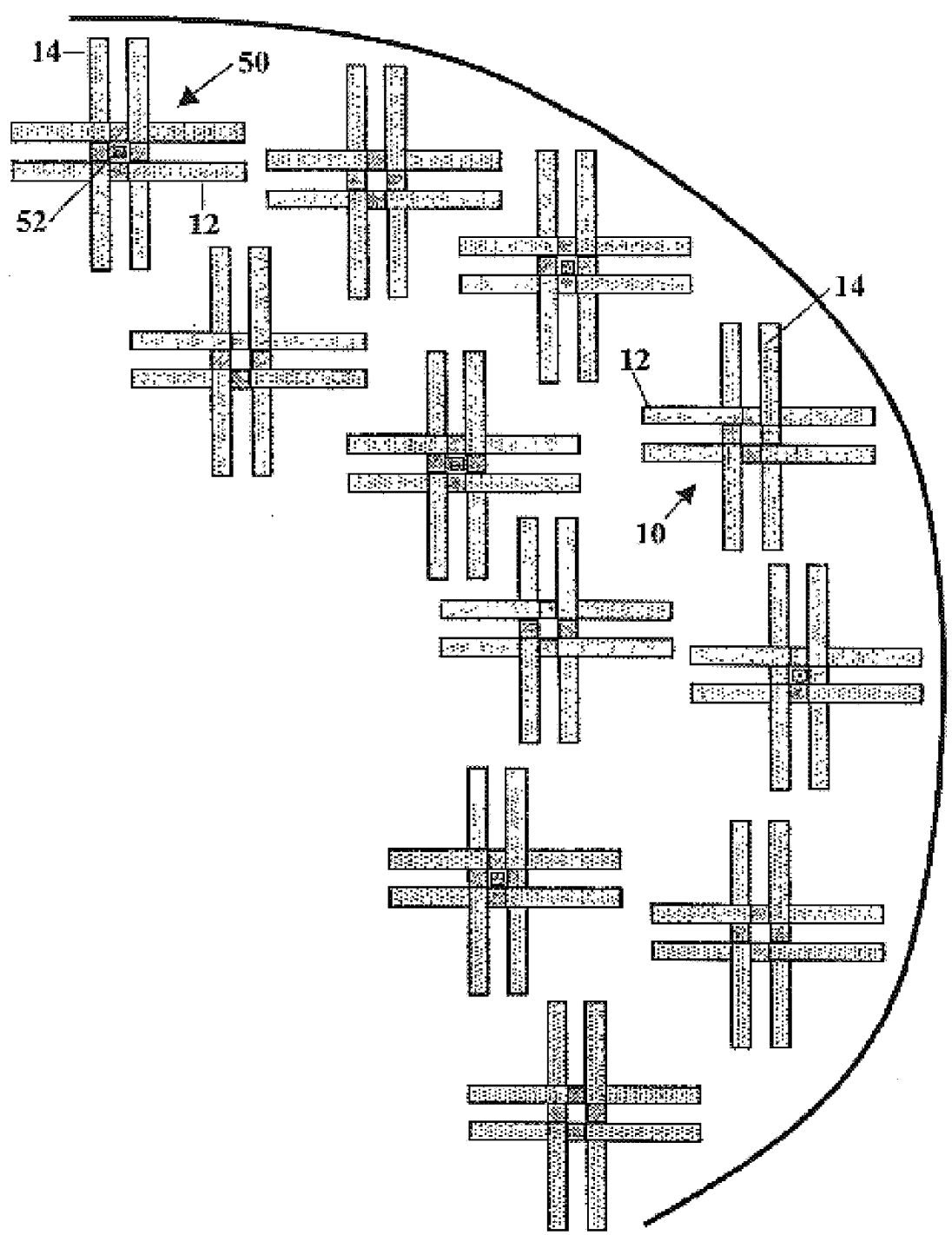

FIGS. 11 and 12 demonstrate other configurations of arrays. FIG. 11 is a schematic diagram of a shifted-row array. The shifted arrangement shown in FIG. 11 increases spatial resolution of the field mapping, if the array is scanned over the area to be mapped in a direction orthogonal to the direction of rows. FIG. 12 is a schematic of an arbitrarily-shaped array. This arbitrarily-shaped array would be useful for mapping electromagnetic fields along a contour or edge of a test specimen. Those of ordinary skill in the art will now recognize that the shifted-row array, and the arbitrarily-shaped array, could comprise two dimensional sensors, three-dimensional sensors, or a combination of two- and three-dimensional sensors.

Figure 13:
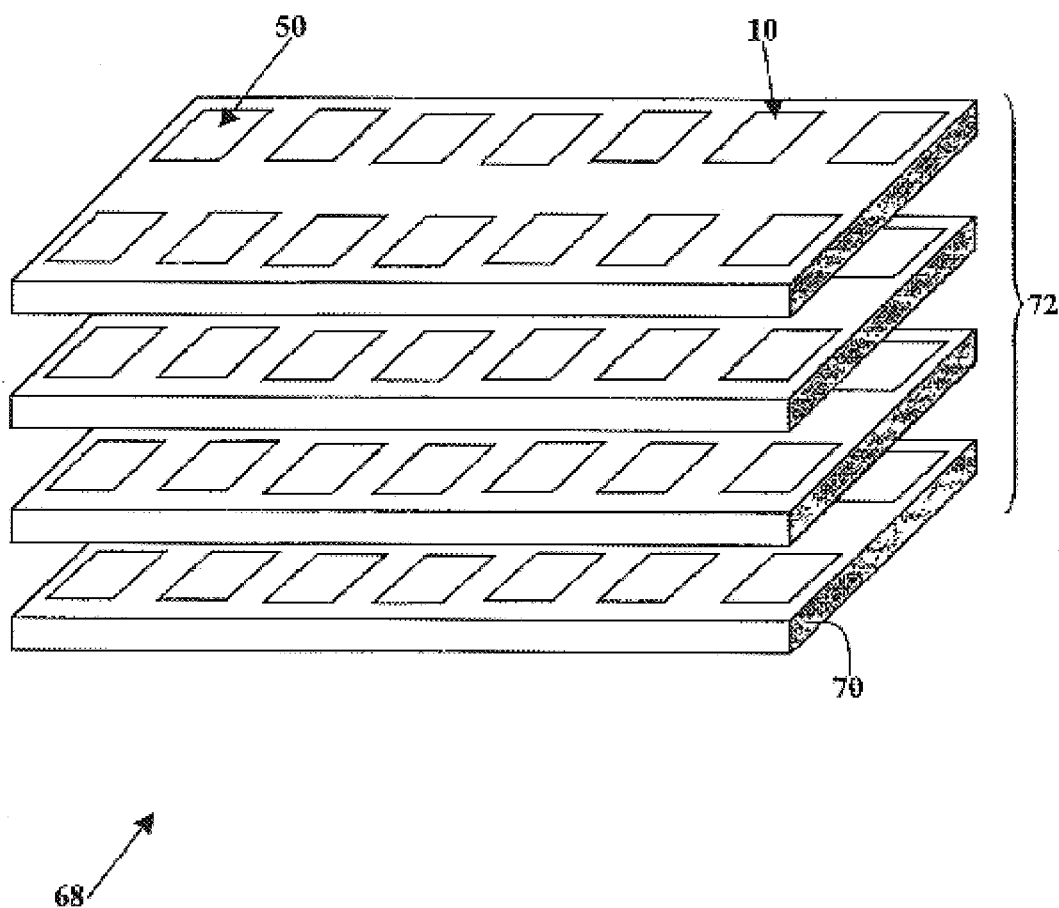
FIG. 13 is a schematic drawing of a sensor stack.

FIG. 13 is a schematic drawing of a sensor stack 68. Because the sensors shown in FIGS. 1–8 may be formed on semi-conductive substrates, the present invention is particularly suited to stacked arrangements of sensors and sensor arrays. As FIG. 13 shows, a plurality of the two-directional sensor 10, or the three-directional sensor 50, may be formed on a substrate 70. Multiple substrates, having similar pluralities of sensors, may be arranged in a stack 72. The stack 72 is very useful for mapping volumes and complex, three-dimensional configurations. The stack 72, moreover, reduces the effects of sensor defects. If a single sensor is defective, then multiple, stacked sensor arrays provide redundancy.

Thus far we have discussed various configurations of two directional and three directional sensors. The sensors isolate and measure individual vector components of electromagnetic fields within a localized area. These sensor configurations may utilize giant magneto-resistive (GMR) sensors, geometric magnetoresistance sensors, spin-dependent tunneling (SDT) sensors, anisotropic magneto-resistive (AMR) sensors, and Hall effect sensors. We have used various configurations of these sensors in laboratory testing. We now show results of our tests so that those of ordinary skill can make and use our sensor invention.

EXAMPLES

Figure 14:
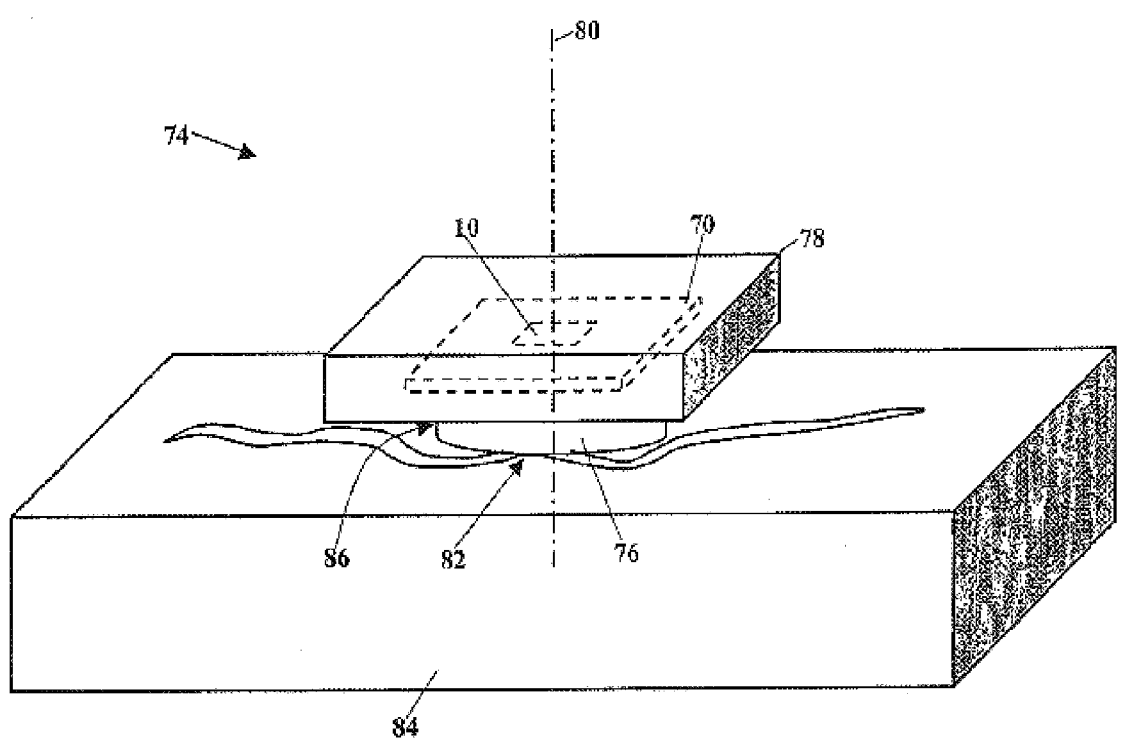
FIG. 14 is a schematic drawing of an eddy current probe.

The sensors of the present invention are further illustrated by the following non-limiting examples. These non-limiting examples describe various eddy current probes utilizing the sensors of the present invention. Eddy current probes are used to detect cracks in electrically conductive materials. An eddy current probe, more specifically, induces eddy currents in a specimen, and the probe detects perturbations in the induced eddy currents. The perturbations indicate a crack is present FIG. 14 is a schematic drawing of an eddy current probe 74. The probe 74 may comprise a flat, pancake-style coil 76 and any sensors shown in FIGS. 1–8. The probe 74, for simplicity, is shown comprising a solid-state sensor package 78. The sensor package 78 is shown containing the substrate 70, as shown in FIG. 13. At least one sensor 10 is shown formed on the substrate 70. The sensor package 78 is coaxially located along a coil axis 80 and adhesively bonded to the coil 76. The coil 76 has a first end 82 near an electrically conductive specimen 84. The coil 76 has an opposite second end 86 distal from the specimen 84. As FIG. 14 shows, each sensor 10 is arranged exterior to the coil second end 86. This arrangement, with the first end 82 near the specimen 84 and the sensor 10 exterior to the second end 86, provides the possibility of reducing the diameter of the excitation coil 76, thus increasing the spatial resolution of the eddy current probe. Because the coil 76 is placed closest to the specimen 84, the induced electromagnetic field is greatest. As the coil 76 is displaced from the specimen 84, the induced electromagnetic field decreases rapidly. The best resolution is experimentally attained when the coil 76 is placed nearest to the specimen 84. While the coil 76 is shown as a flat, pancake-style coil, other coil geometries, such as a circularly-shaped configuration, are also suitable. Those of ordinary skill in the art also recognize that the two-directional sensor 10 could utilize giant magneto-resistive (GMR) sensors, spin-dependent tunneling (SDT) sensors, and/or anisotropic magneto-resistive (AMR) sensors. Probes utilizing one-directional or three-directional sensors could also be used. The coil 76 could have a cylindrical configuration and surround the sensor package 78. A probe utilizing a one-directional SDT sensor, for example, could include a flat pancake coil.

The probe 74 is used to scan the surface of the specimen 84. The coil 76 is placed above the surface of the specimen 84, with the coil axis 80 perpendicular to the surface of the specimen 84. For optimal operation the sensitive axis of the sensor 10 is coplanar with the surface of the specimen 84 and, therefore, perpendicular to the coil axis 80. When the specimen 84 is defect-free, the electromagnetic field created by the coil 76 produces circular eddy currents in the specimen 84. In this case, the signal detected by the sensor 10 is zero, because the excitation field and the field created by the eddy current are normal to the sensitive axis of the sensor 10. If a defect is present, this defect will obstruct the current flow, causing it to deviate from its circular path. The perturbation of eddy currents produces a field that is detected by the sensor 10.

Figure 15:
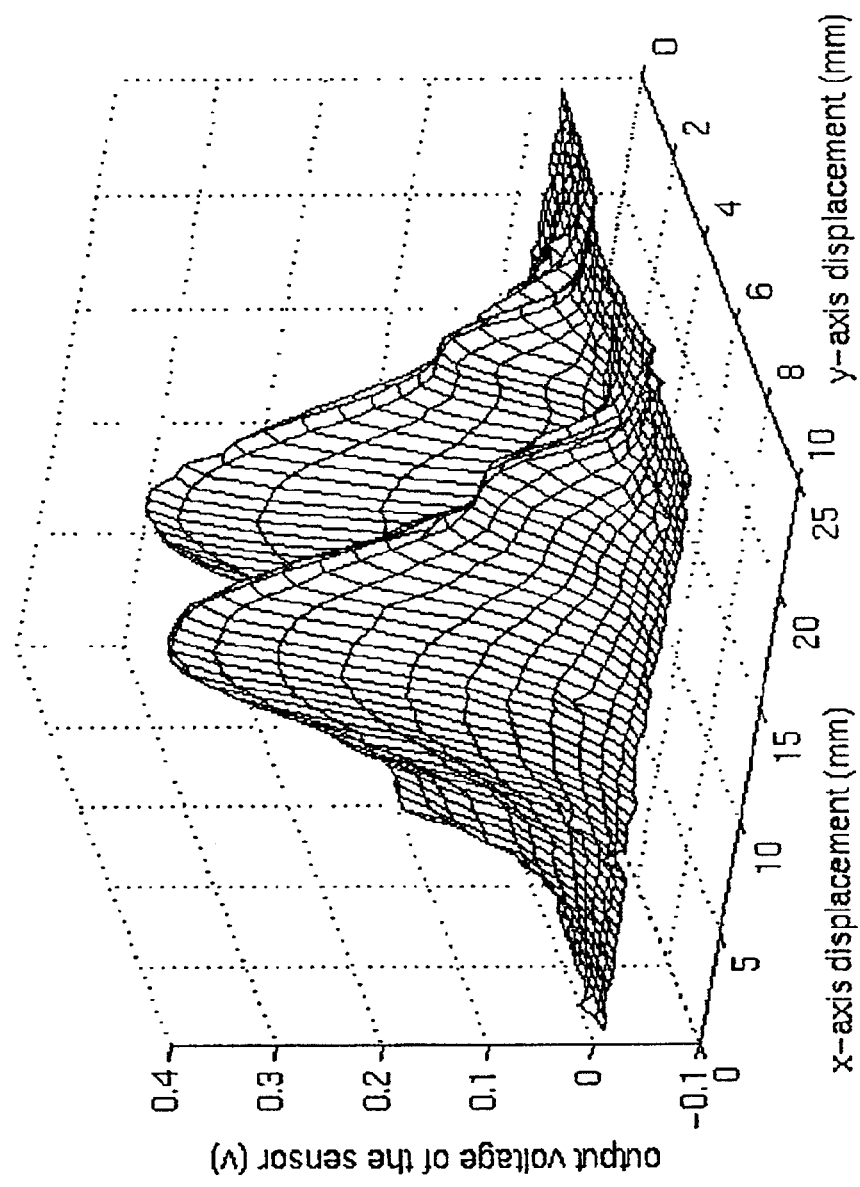
FIGS. 15 and 16 are graphs of the output of the eddy current probe shown in FIG. 14.
Figure 16:
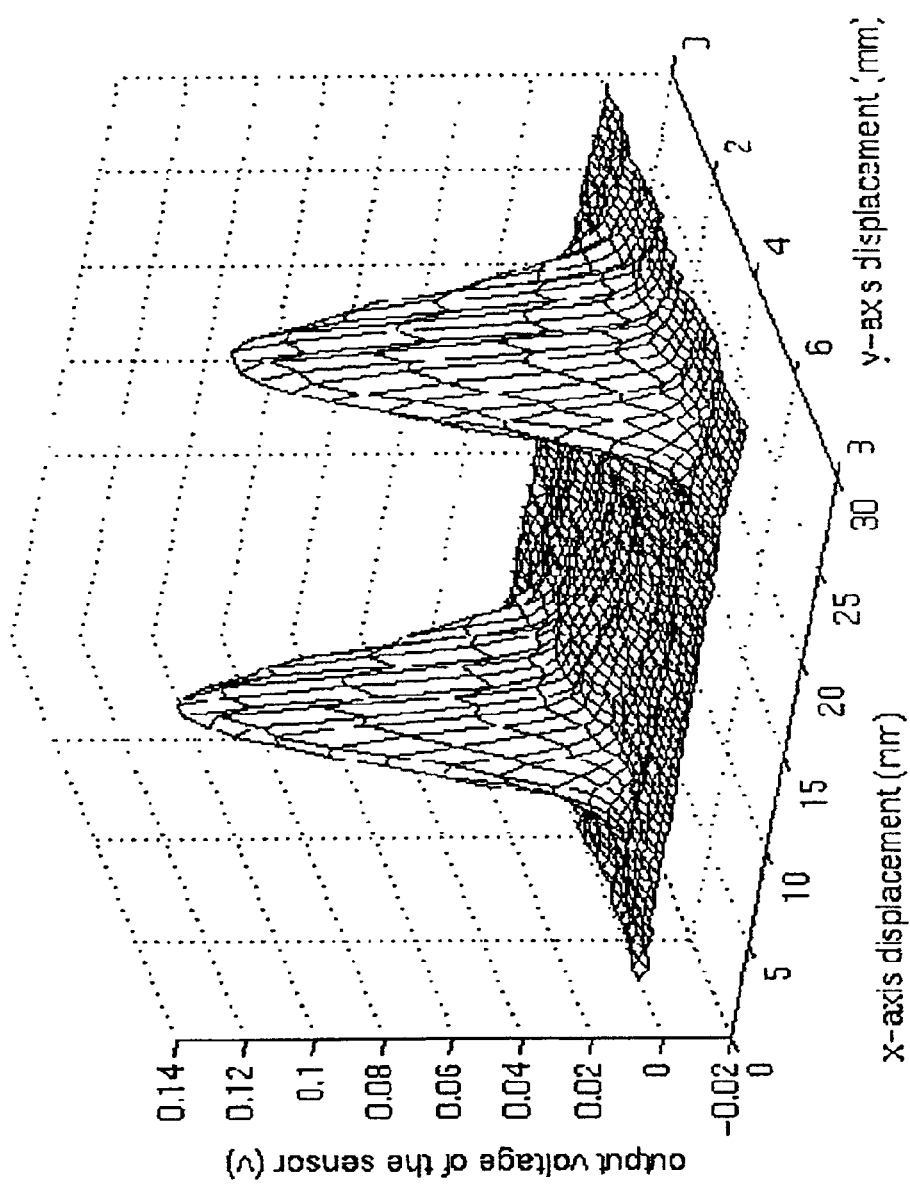

FIGS. 15 and 16 are graphs of the output of the eddy current probe 74 shown in FIG. 14. The graphs were produced when the probe scanned a crack of fifteen millimeters (15 mm) in length. FIG. 15 shows the magnitude of the probe output when the sensitive axis of the sensor 10 is oriented perpendicular to the crack direction. The sensor 10 has maximum sensitivity when the sensitive axis of the sensor 10 is oriented perpendicular to the crack direction. As FIG. 15 shows, the crack is located between coordinates (5,4) and (20,4). FIG. 16 shows if the sensitive axis is rotated with respect to the crack direction, the shape of the two peaks on either side of the crack is distorted and the signal magnitude diminishes. When the axis is oriented parallel to the crack, after a rotation of ninety degrees (90°), the signal from the sensor 10 is reduced and two peaks are located around the tips of the crack.

The orientation of the sensor 10 relative to the crack direction affects the output signal from the sensor 10 on each direction. The magnitude of an in-plane electromagnetic field vector may be calculated as $$|B|=\sqrt{B_x^2+B_y^2}$$

where x and y are the directions of the sensitive axes of the two orthogonal sensors. The superimposed maps of $B_x$ and $B_y$ will result in a more complex map of $|B|$. The resulting map of $|B|$ contains two major peaks, disposed on the sides of the crack, and two smaller peaks at the ends of the crack. For an arbitrary crack orientation, the map of $|B|$ is automatically rotated such that the two major peaks are parallel to the crack orientation. This represents a method for determining the orientation of a randomly oriented crack, by plotting the map of the in-plane vector magnitude of the electromagnetic field.

For detecting cracks that grow from an edge (hereafter referred to as edge-cracks), the parallel orientation of the sensitive axis of one sensor with the edge is essential. Plotting the map of $|B|$ is not a solution, because, in this case, due to the large signal produced by the edge, the superposition of the signals in perpendicular directions will mask the crack. In this case, a preliminary scan in the edge region is recommended. Once the orientation of the edge is determined from the in-plane vector magnitude $|B|$ map, the probe can be rotated such that the axis x is aligned parallel (or tangential) to the edge. In this way, the sensor sensitive along the x-axis is insensitive to the presence of the edge. Consequently, a new scan is performed, this time monitoring only the output of the sensor sensitive along the x-axis. The $B_x$ map produced by this sensor enables the detection of cracks that initiate from the edge, whereas the edge signal is eliminated.

For accurate results, the coil (shown as reference numeral 76 in FIG. 14) needs to be aligned with respect to the two-directional sensor 10, such that the field induced by the coil 76 is both perpendicular and centered about the sensitive area. The alignment problem is avoided if the coil 76 is deposited directly on the same substrate as the magneto-resistive sensors (shown as reference numerals 12 and 14 in FIG. 1). Using photolithographic process, the masks for the coil 76 and for the magneto-resistive sensors can be precisely aligned within the errors of the process. Thick film spiral coils, for example, can be deposited directly on the same substrate with the magneto-resistive sensors. Ideally the deposited coil should have rotational symmetry. The deposited coil may contain two (or a multiple of two) layers of winding overlaid on top of each other and insulated by silica (or any other electrical insulator).

The probe 74 (again shown in FIG. 14) was also used to demonstrate the mapping of a randomly-oriented crack. Here the probe, using a two-directional GMR sensor, was used to determine the direction of a crack of random orientation in a conductive test specimen. The sensitive plane of the GMR sensor is parallel to the test specimen surface. The two-directional GMR sensor measures the two orthogonal components of the magnetic field essentially at the same point within the plane of the sensor. The probe included a flat pancake coil placed on top of the sensor, parallel to the sensor's plane, and centered about the point where the two-dimensional field is to be measured. The flat pancake coil had a one millimeter (1 mm) internal diameter, a 3.4 mm external diameter, a thickness of 0.2 mm, and twenty four (24) turns of 0.1 mm diameter wire. A sinusoidal current, of 2 A at 100 kHz, flowed through the wire. The amplitude from each GMR sensor, on each orthogonal axis, was extracted using two lock-in amplifiers, both locked on the excitation signal. The two-dimensional vector amplitude was computed from the two orthogonal components. The probe was then scanned over a surface crack of length 5 mm, of width 0.15 mm, and of depth 0.5 mm.

Figure 17A:
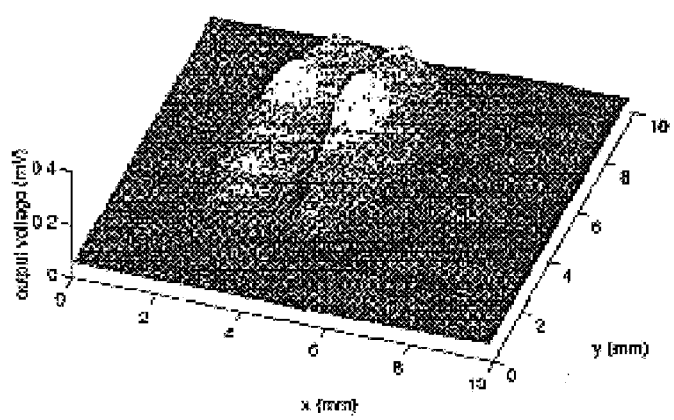
FIGS. 17A, 17B, and 17C show maps when one sensing axis is approximately parallel to the crack orientation.
Figure 17B:
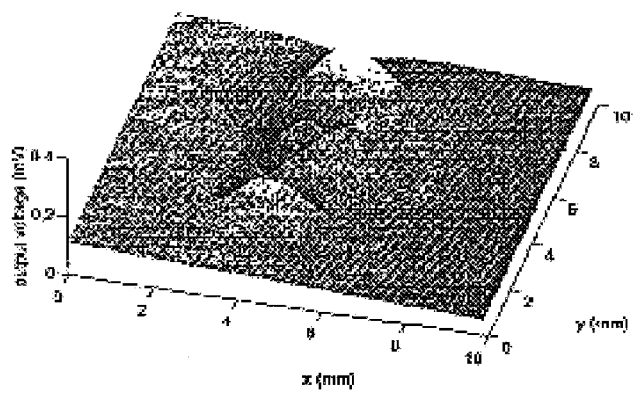
Figure 17C:
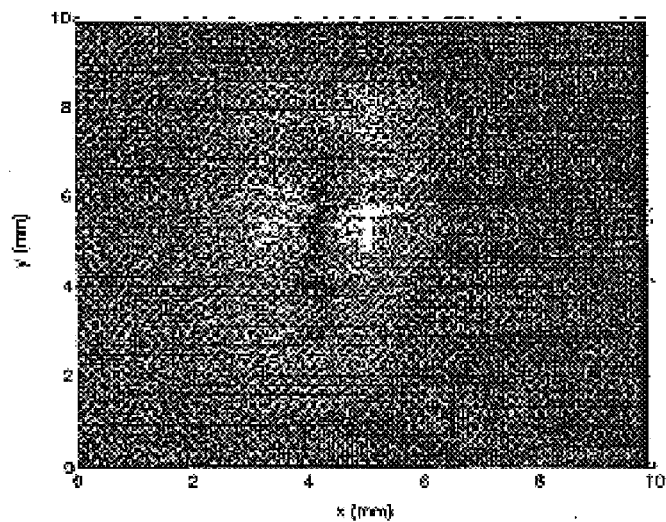

FIGS. 17A, 17B, and 17C show maps when one sensing axis is approximately parallel to the crack orientation. Because the two GMR sensors are orthogonally oriented, the other sensing axis is perpendicular to the crack orientation. FIG. 17A shows a map produced from the output magnitude of the sensor having a sensitive axis oriented perpendicular to the crack. FIG. 17B shows a map produced from the output magnitude of the sensor having a sensitive axis oriented parallel to the crack. FIG. 17C is a two-dimensional map produced from the magnitude of the vector sum of the output magnitudes shown in FIGS. 17A and 17B.

Figure 18A:
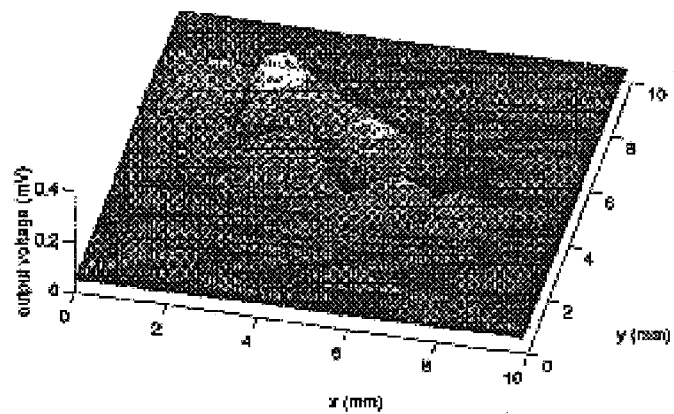
FIGS. 18A, 18B, and 18C demonstrate that a two-directional sensor can accurately map a randomly-oriented crack.
Figure 18B:
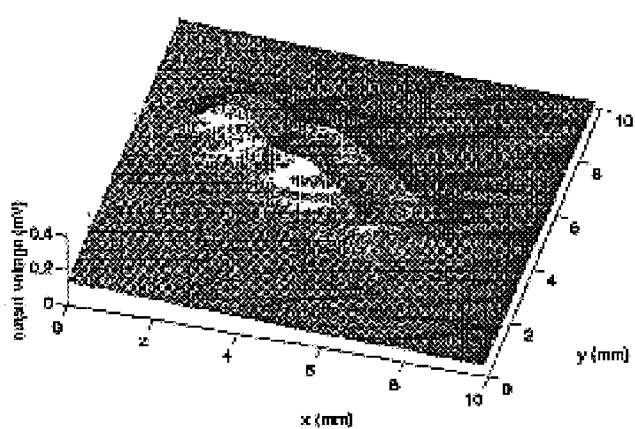
Figure 18C:
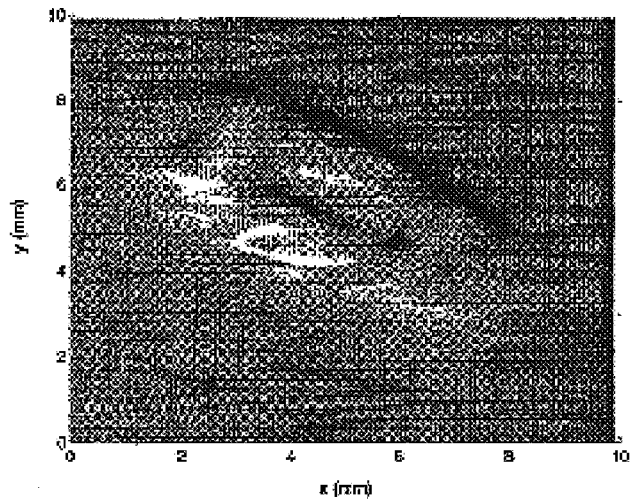

FIGS. 18A, 18B, and 18C demonstrate that a two-directional sensor can accurately map a randomly-oriented crack. Here the crack was rotated sixty degrees (60°) counterclockwise and scanned using the same two-directional GMR sensor. FIG. 18A is a map produced from the output magnitude of the sensor, with the sensor's sensitive axis oriented sixty degrees (60°) to the longitudinal axis of the crack. FIG. 18B, likewise, is a map produced from the output magnitude of the sensor, with the sensor's sensitive axis oriented 150° to the longitudinal axis of the crack. FIG. 18C is a two-dimensional map produced from the magnitude of the vector sum of the fields shown in FIGS. 18A and 18B. Although the maps of a randomly-oriented crack are not as easily interpreted, these experiments demonstrate that a two-directional sensor can accurately map straight cracks having an arbitrary orientation. While these experiments utilized GMR sensor technology, those of ordinary skill now recognize that spin-dependent tunneling (SDT) sensors and anisotropic magneto-resistive (AMR) sensors could also be used.

Figure 19:
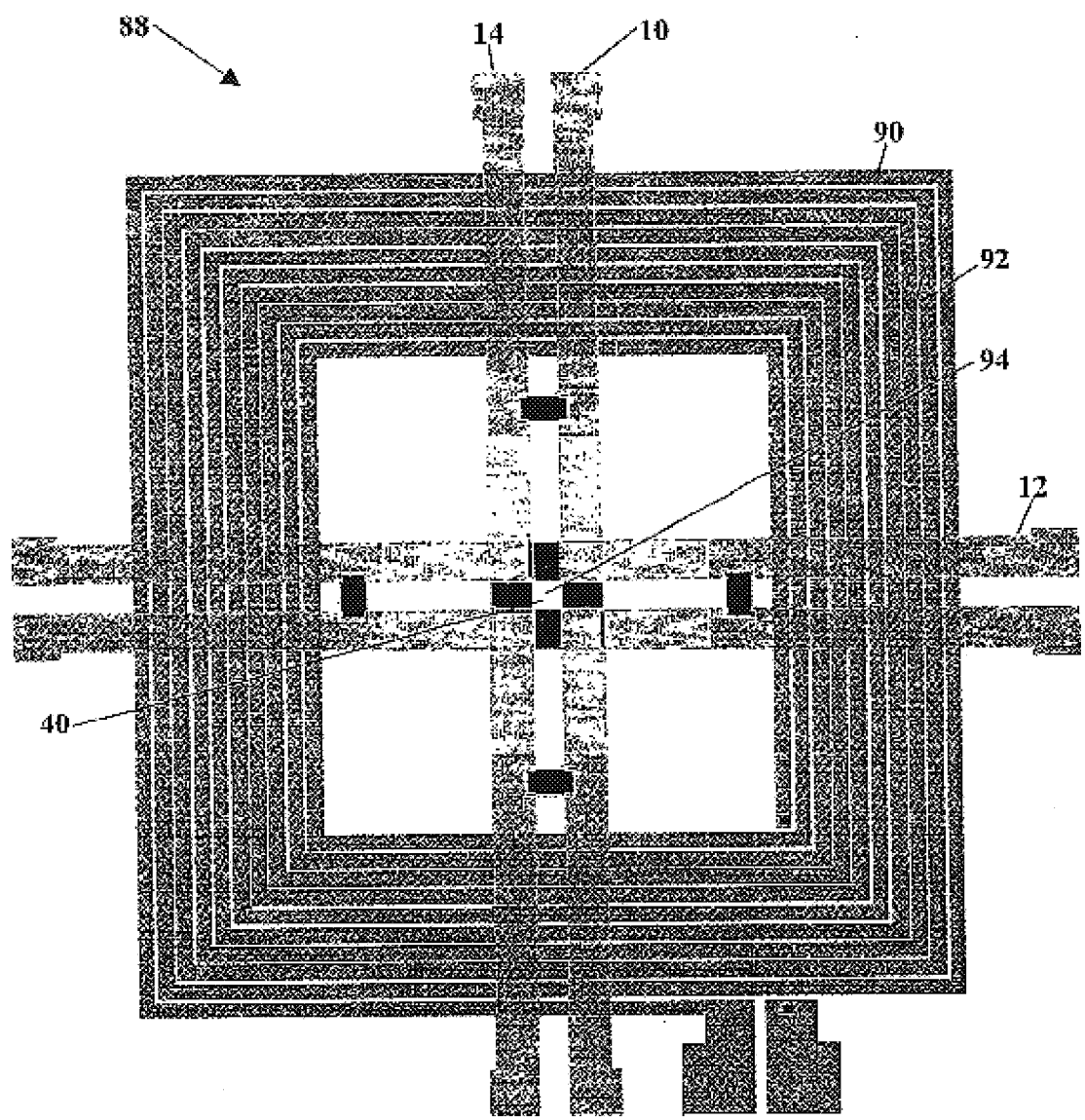
FIG. 19 is a schematic drawing of an embodiment of an integrated probe.

FIG. 19 is a schematic drawing of an embodiment of an integrated probe 88. The integrated probe 88 comprises the sensor 10 and an integrated coil 90. The integrated coil 90 would preferably have a two-layer design. Current would flow through a top layer 92 and continue on to a bottom layer. The current, however, would flow in the same direction in each layer. Because current flows in the same direction, the magnetic fields created by the top layer 92, and by the bottom layer, add in a center 94 of the integrated coil 90 (in a direction perpendicular to a plane of the integrated coil 90). The thickness of the traces should be designed as a function of the maximum current that can pass through the integrated coil 90. One drawback of the square-shaped coil shown in FIG. 19 is that it does not have circular symmetry about its center. A better design that can be easily implemented in the planar technology (by photolithography) is an octagonal shape. A circular spiral coil is also an alternative, but a spiral design has thus far proven more difficult to implement in integrated technology. A circular two-layer spiral coil can be separately manufactured by manual or automated winding. This coil can be subsequently attached to the bi-directional sensor resulting in a compact eddy current probe.

A one-layer spiral coil can be also used as integrated excitation coil. One end of the coil is accessed through a pad placed at the interior of the spiral. One disadvantage of this one-layer spiral design is that the bonding wire connected to the pad, and also near the magneto-resistive sensor, may produce a significant magnetic field. This component of the excitation field effects the signal detected by the magneto-resistive sensor and, thus, reduces the accuracy of crack detection.

Figure 20A:
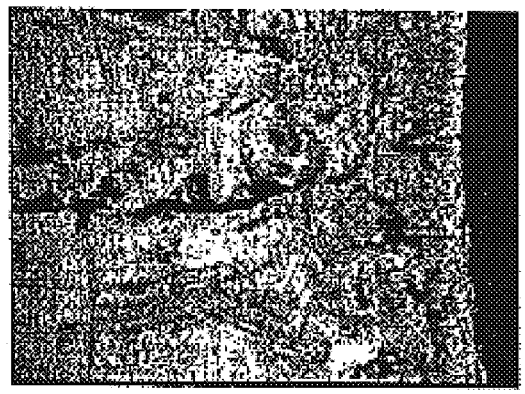
FIGS. 20A, 20B, and 20C show the capabilities of the unidirectional SDT-based probe.
Figure 20B:
Figure 20C:
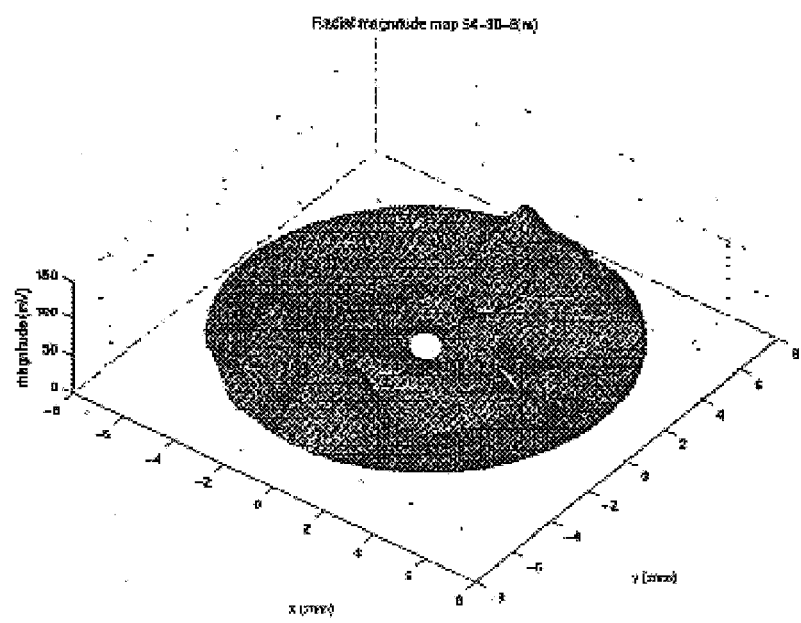

FIGS. 20A, 20B, and 20C show the capabilities of the unidirectional SDT-based probe. The magneto-resistive sensor designs of the present invention were used in the mapping of cracks on the periphery of holes in aluminum plates. This is a typical defect encountered in aerospace applications. FIGS. 20A and 20B are magnified photos of two cracks initiating on opposite sides of a hole. Because the cracks were not visible to the naked eye, the photos were taken using an optical microscope. Eddy current testing was performed by scanning the probe over a ring containing the edge of this hole. FIG. 20C shows a three-dimensional map indicating the output voltage of the probe, as a function of x-y position above the specimen. FIG. 20C shows two pairs of peaks which correspond to the presence of a crack. The crack can be precisely located between these pairs of peaks. The results demonstrate the capability of using magneto-resistive sensors to obtain images for the detection and location of cracks initiating on the edge of riveted holes.

Figure 21:
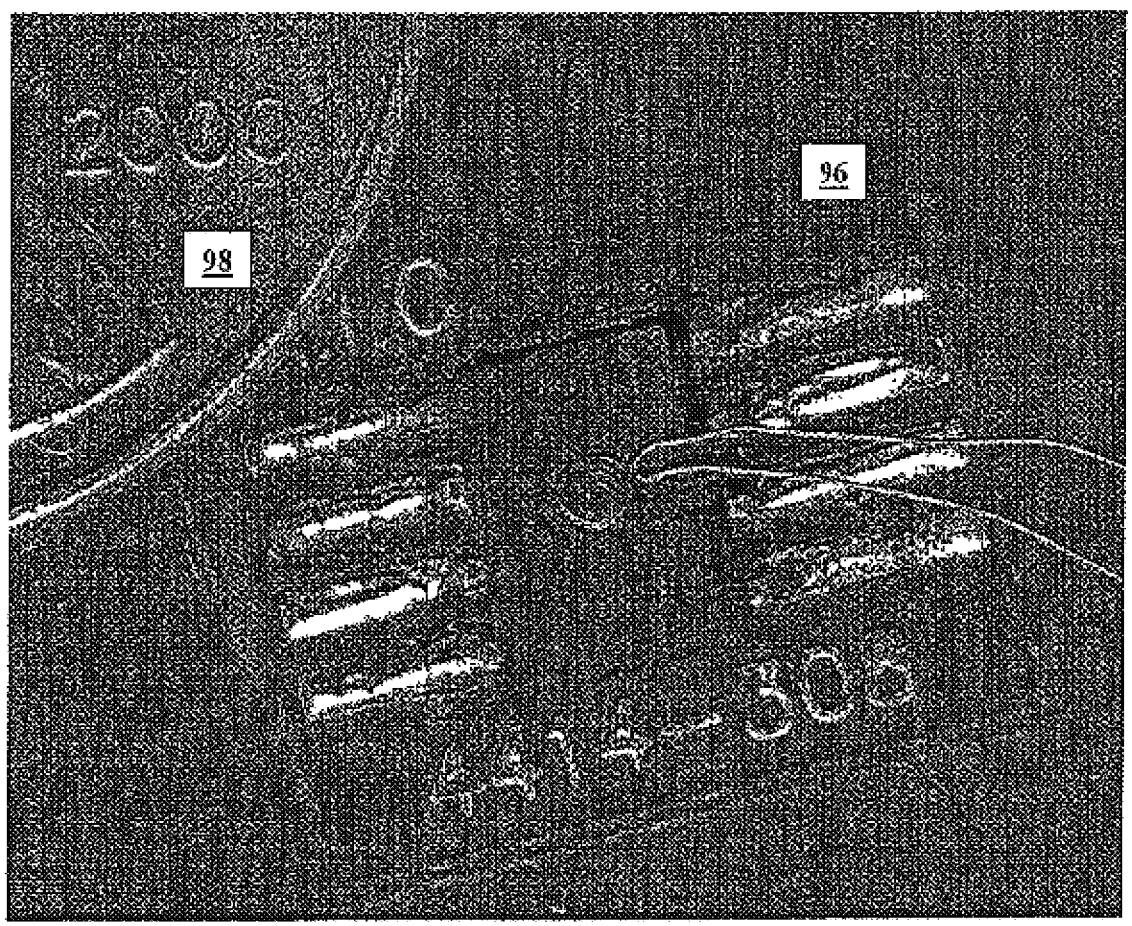
FIGS. 21 and 22 demonstrate the resolution of the sensors and probes described herein.

FIGS. 21 and 22 demonstrate the resolution of the sensors and probes described herein. An eddy current probe 96, utilizing the sensors of the present invention, was used to scan a United States penny 98. FIG. 21 is a magnified photo showing both the details of a probe 96 and the relative size of the probe 96 to the penny 98. The probe 96 comprised a two-directional sensor and a flat, pancake coil disposed on top of the sensor. As this patent mentioned earlier, the resolution of an eddy current probe, in general, is closely related to the diameter of the excitation coil. During this study coils of diameter down to 0.65 millimeter have been produced and mounted onto a two-directional giant magneto-resistive sensor.

For this application only very small diameter excitation coils are necessary. A series of flat pancake-type coils ranging from 0.65 millimeter to two millimeters (0.65 mm to 2 mm) external diameter were manufactured at The University of North Carolina at Charlotte. The coils comprise ten (10) to twenty (20) turns of 0.075 millimeter diameter bondable copper wire manually wounded around a 0.2 mm brass shaft. After the coils were wound, the coils were heated using a heat gun to bond the wires together. Very regular and reproducible, two-layered coils were obtained using this procedure. The coil shown in FIG. 21 was produced using this method.

A two-directional giant magneto-resistive sensor was used. The giant magneto-resistive sensor was manufactured by NVE Corporation, part number AA002. To reduce the lift-off between the sensors and the surface of the coin 98, a thin layer of the top of the sensors package has been removed using a milling cutter. A small flat bottomed hole, slightly larger than the diameter of the excitation coil, was machined in the middle of the sensor package. The depth of this hole coincides to the height (0.15 mm) of the flat coil. A recess has also been machined for the wires delivering current to the coil. The coil afterwards was inserted in the flat bottomed hole. The coil is automatically aligned parallel to the surface of the sensor package. To obtain a good centering of the coil on the sensor package, a sinusoidal excitation current was applied to the coil, and the output of both sensors in orthogonal directions was monitored. The position of the sensor package was manually adjusted until the maximum attenuation of sinusoidal signals at both outputs is observed (ideally the field sensed by the centered sensor package would be zero). Once the center position was found, the coil was glued to the sensor package.

Figure 22A:
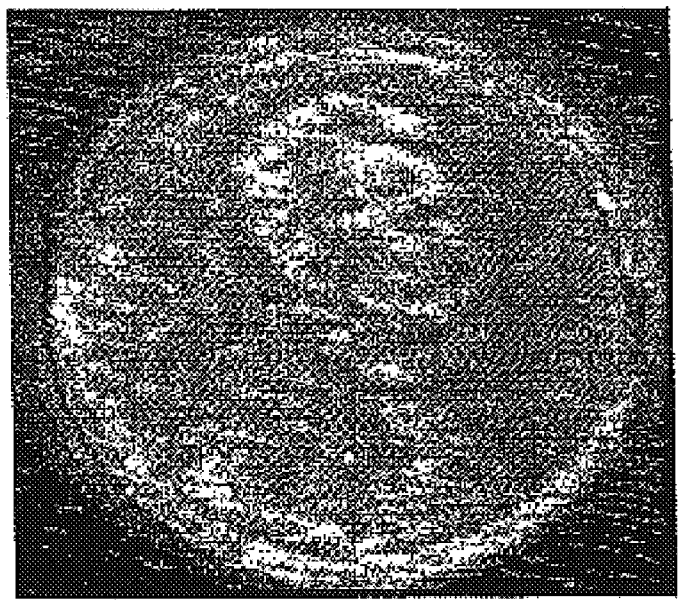
Figure 22B:
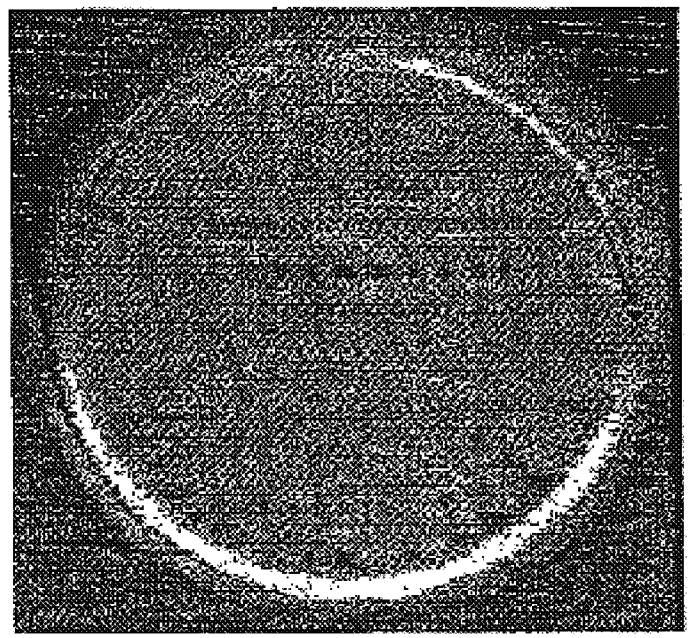

FIGS. 22A and 22B are maps of the probe output for both sides (or faces) of the penny (shown as reference numeral 98 in FIG. 21). The map of the coin profile was obtained by scanning the probe 96 over the coin 98 using a coordinate measuring machine. Consequently two maps of the coin 98 were obtained, corresponding to the two orthogonal components of the magnetic field in the plane of the coin 98. A sinusoidal current of 1.3 A amplitude at a frequency off f=100 kHz was passed through the excitation coil. The lift-off separation between the coil and the surface of the coin 98 was 0.1 mm. Data points were measured using a square grid, with steps of 0.1 mm in both directions, such that 250×250 pixels (data points) were obtained for each 25 mm×25 mm map. To eliminate the influence of background DC magnetic field, such as earth's magnetic field, the sensor package was biased using a small permanent magnet placed close to the sensor package. The magnet was placed with its principal axis within the plane of the sensor and was oriented at forty-five degrees (45°) with respect to both orthogonal sensitive axis. In this way both orthogonal sensors act as bipolar devices. The signal from the coin 98 can be demodulated using a lock-in amplifier, locked on the excitation frequency. The output signal was also amplified (×10).

This method of coin imaging, unlike optical imaging, enables one to not only image the profile of conductive material, but also, to obtain information on the material itself. This is useful for detecting counterfeit coins. The present invention also allows for quick imaging of coins and for imaging granular structures of different alloys, such as titanium alloys. The present invention also allows monitoring of corrosion with high resolution, on the order of hundreds of micrometers or less.

Figure 23A:
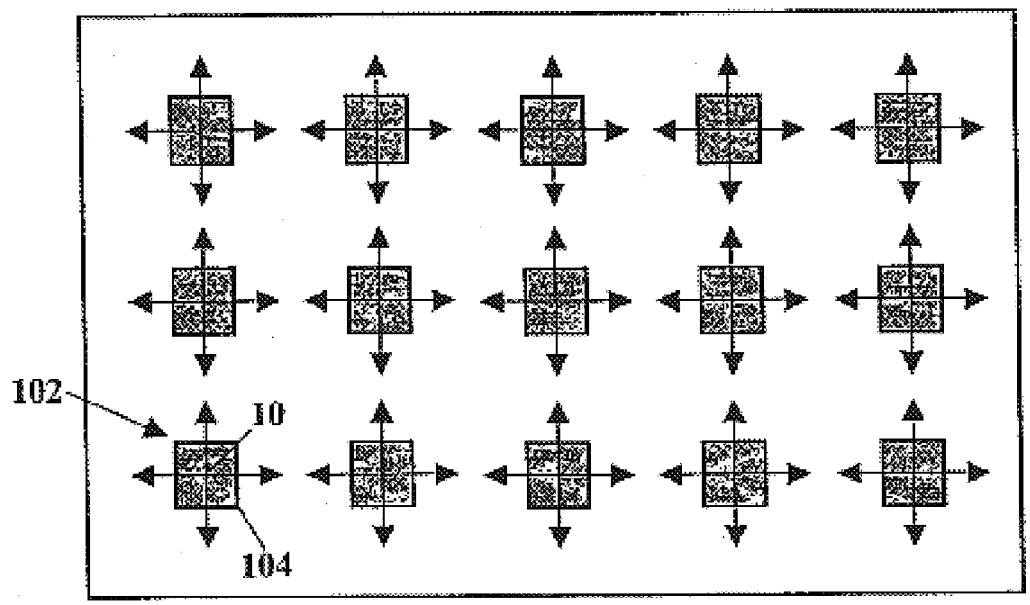
FIGS. 23A and 23B are schematic drawings of an array of probes.
Figure 23B:
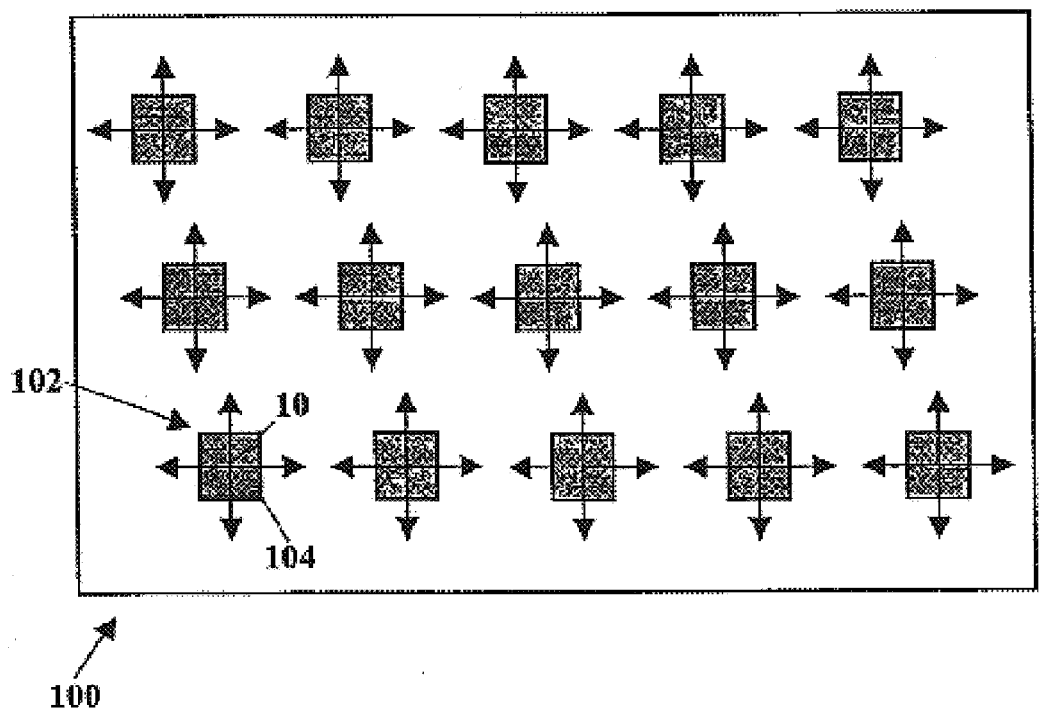

FIGS. 23A and 23B are schematic drawings of an array 100 of probes. Each probe 102 in the array of probes 100 is shown comprising a two-dimensional sensor 10 and an excitation coil 104. FIG. 23A shows the array 100 of probes comprised of an arrangement of equally-spaced rows and columns of probes 102. FIG. 23B, on the other hand, shows an arrangement of shifted rows and columns of probes 102. The shifted arrangement shown in FIG. 23B increases spatial resolution of the field mapping. Those of ordinary skill in the art will now recognize that the array 100 of probes could alternatively comprise three-dimensional sensors or a combination of two- and three-dimensional sensors. Those of ordinary skill in the art also recognize that the array 100 of probes could have any arrangement that is advantageous for mapping a conductive surface. The array 100 of probes, for example, could have a rectangular configuration, a circular configuration, or some arbitrary configuration.

Figure 25:
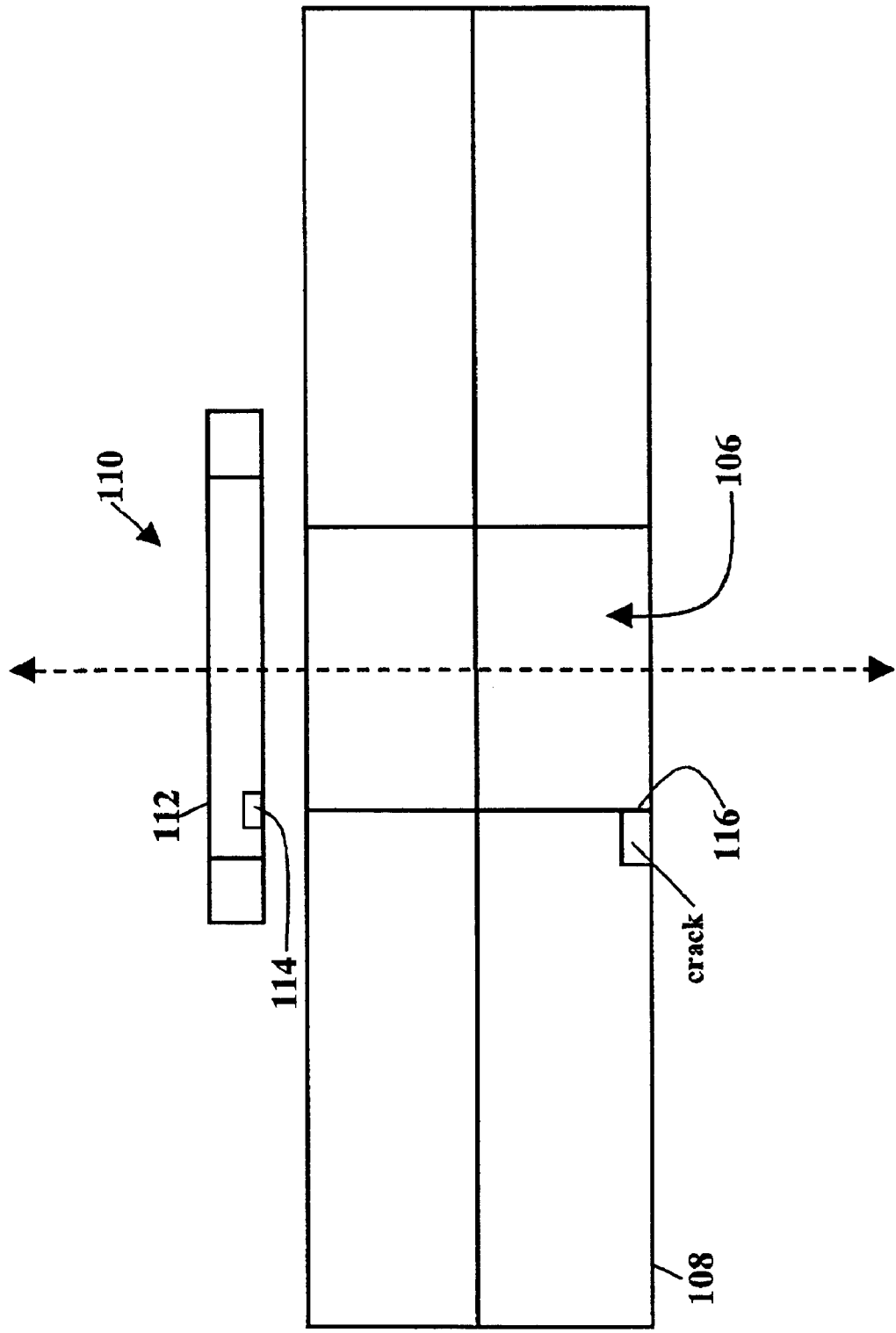

FIGS. 24 and 25 are sectional views of probes demonstrating the use of a circular array of sensors to detect cracks around a fastener hole 106. The fastener hole 106 could be located in a conductive multi-layered structure 108. An eddy current probe 110 comprises a circular excitation coil 112 and an array of spin-dependent tunneling (SDT) magnetoresistive sensors 114. The eddy current probe 110 detects and monitors cracks initiating at an edge 116 of the fastener hole 106. SDT sensors are suitable for this application due to their high sensitivity at low frequencies (necessary for the detection of deeply buried defects) and their small dimensions for high spatial resolution and low cost compared to fluxgate or SQUID sensors. The circular excitation coil 112 is placed above, and concentric with, the fastener hole 106. Each sensor 114, in the array of SDT sensors, is distributed above the circumference of the hole 106, with a sensitive axis oriented tangential to the edged 116 of the hole 106. Depending on the mean radius of the circular coil 112, the coil 112 may be placed above the sensor, as shown in FIG. 24, or external and surrounding the sensor, as shown in FIG. 25. The latter, external design has the advantage that the lift-off between the coil 112 and the multi-layered structure 108 can be minimized. To inspect a hole an AC current is applied to the coil 112. The sensor 114 is rotated along the circumference of the hole 106 while maintaining the tangential orientation, and the amplitude and phase of the detected field is recorded.

If a single sensor 114 is used within the eddy current probe 110, the eddy current probe 110 (or only the sensor 114) must be rotated about a center of the hole 106. A multiple sensor array, distributed around a circumference of the hole 106, will reduce the inspection time in proportion to the number of the sensors in the array. A sufficiently dense array can totally eliminate the mechanical circular scan. The proposed eddy current probe 110 addresses the need for non-contacting, rapid inspection using distributed sensors and for highly sensitive devices for detection of buried cracks under bolts.

Figure 26A:
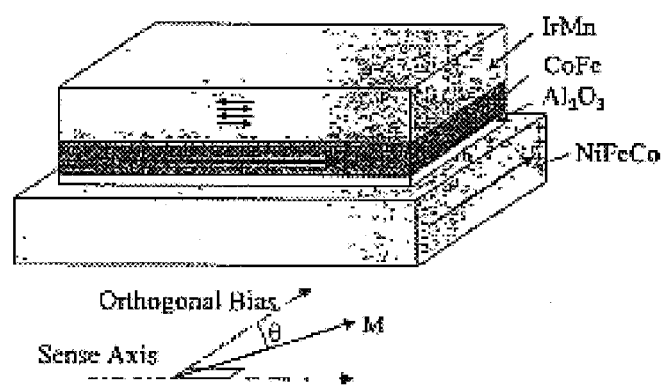
FIGS. 26–29 explain SDT sensor technology.

SDT structures are a recent addition to the materials exhibiting giant magnetoresistive characteristics. FIG. 26A is a schematic showing the structure of a spin dependent tunneling resistor manufactured using thin-film deposition and photolithography. In SDT structures an insulating layer separates two magnetic layers. Conduction is allowed by quantum tunneling through the insulator. The size of the tunneling current between the two magnetic layers is modulated by the angle between the magnetization vectors in the two layers. The direction of magnetization of the bottom NiFeCo layer is free to follow the applied magnetic field. The top CoFe layer is pinned to the adjacent antiferromagnetic IrMn layer and is referred to as the pinned layer. The addition of an orthogonal bias field perpendicular to the direction of the magnetization of the pinned layer reduces hysteresis and results in a bipolar sensor. With no applied field the direction of magnetization of the free layer is perpendicular to that of the pinned layer. Fields along the sense axis parallel to the pinned layer decrease that angle making the layers more parallel and decrease the resistance. Fields in the opposite direction increase the angle and increase the resistance.

Changes of resistance with magnetic field of ten percent to forty percent (10% to 40%) have been observed. The field required for maximum change in resistance depend upon the composition of the magnetic layers and the method of achieving antiparallel alignment. Values of saturation field range from 0.1 to 10 kA/m (1.25 to 125 Oe) offering at the low end, the possibility of extremely sensitive magnetic sensors.

Figure 26B:
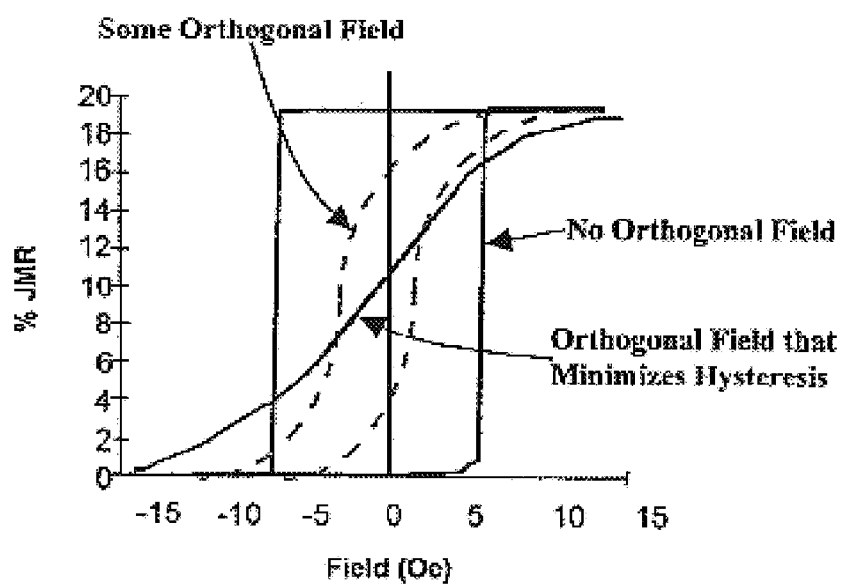

FIG. 26B is a graph of the response from an SDT junction. The outside rectangular trace is for a junction with no orthogonal field. The dashed line shows the junction sensor with some orthogonal field but not enough to eliminate the hysteresis. Finally the inside diagonal curve shows the junction with enough orthogonal field to minimize hysteresis. The orthogonal field decreases the slope gain of the junction, but makes it a much easier to use in a sensor.

Figure 27:
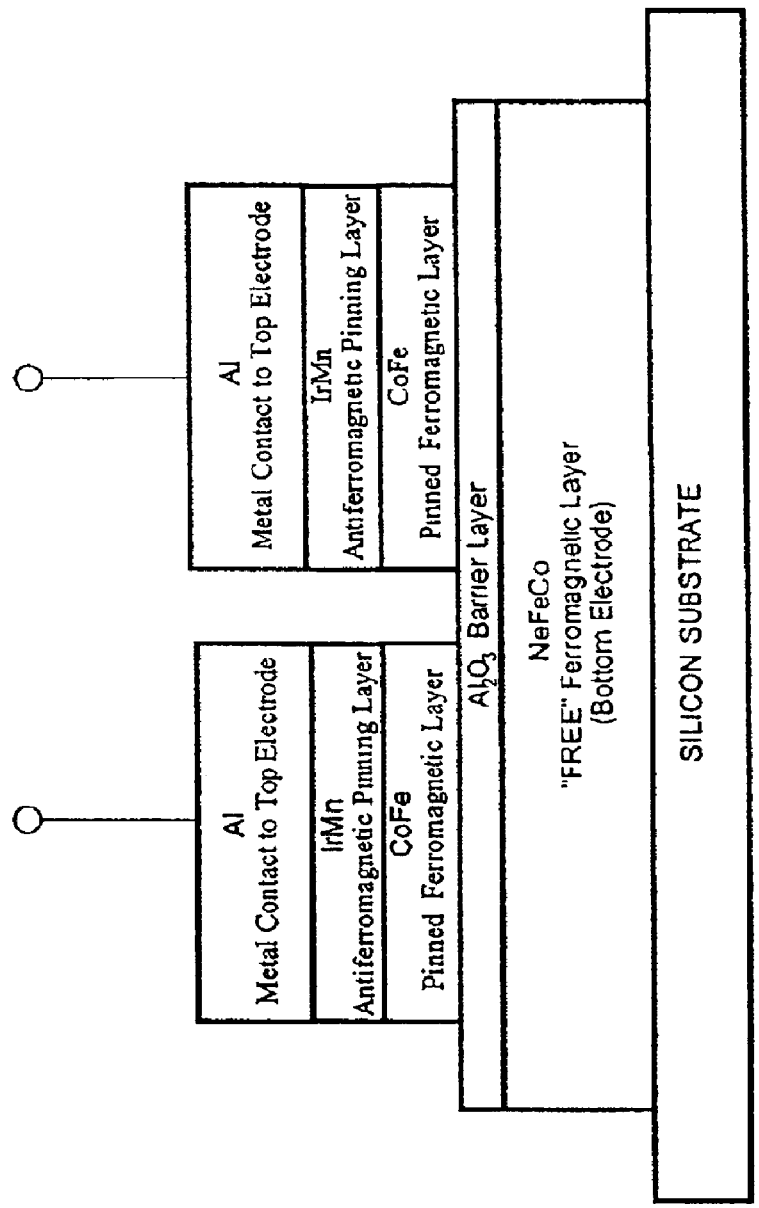

FIG. 27 is a sectional view of an etched pair of SDT junctions. The insulating, tunneling layer provides inherently high resistance sensors suitable for battery operation. Extremely small SDT devices several micrometers on a side with high resistance can be fabricated using photolithography allowing very dense packing of magnetic sensors in small areas. The insulating junction can withstand less than a volt; therefore, several SDT junctions are connected in series for higher voltage operation. Two top layers are etched on common insulating and bottom layer. The external connections are made to the two top layers for a two-junction series element.

The SDT junctions are connected in a Wheatstone bridge configuration to make an SDT sensor. Several junction pairs are connected in series for each arm of the bridge. Plated NiFe bodies serve to concentrate the magnetic field on two of the bridge arms. The junctions forming the other two bridge arms are placed under the NiFe flux concentrators effectively shielding them from the applied field and allowing them to act as reference resistors. An on-chip coil provides the orthogonal field mentioned before to reduce hysteresis. An additional on-chip coil can provide a field parallel to the sensing direction to center the sensitive portion of the response curve or provide feedback.

Figure 28:
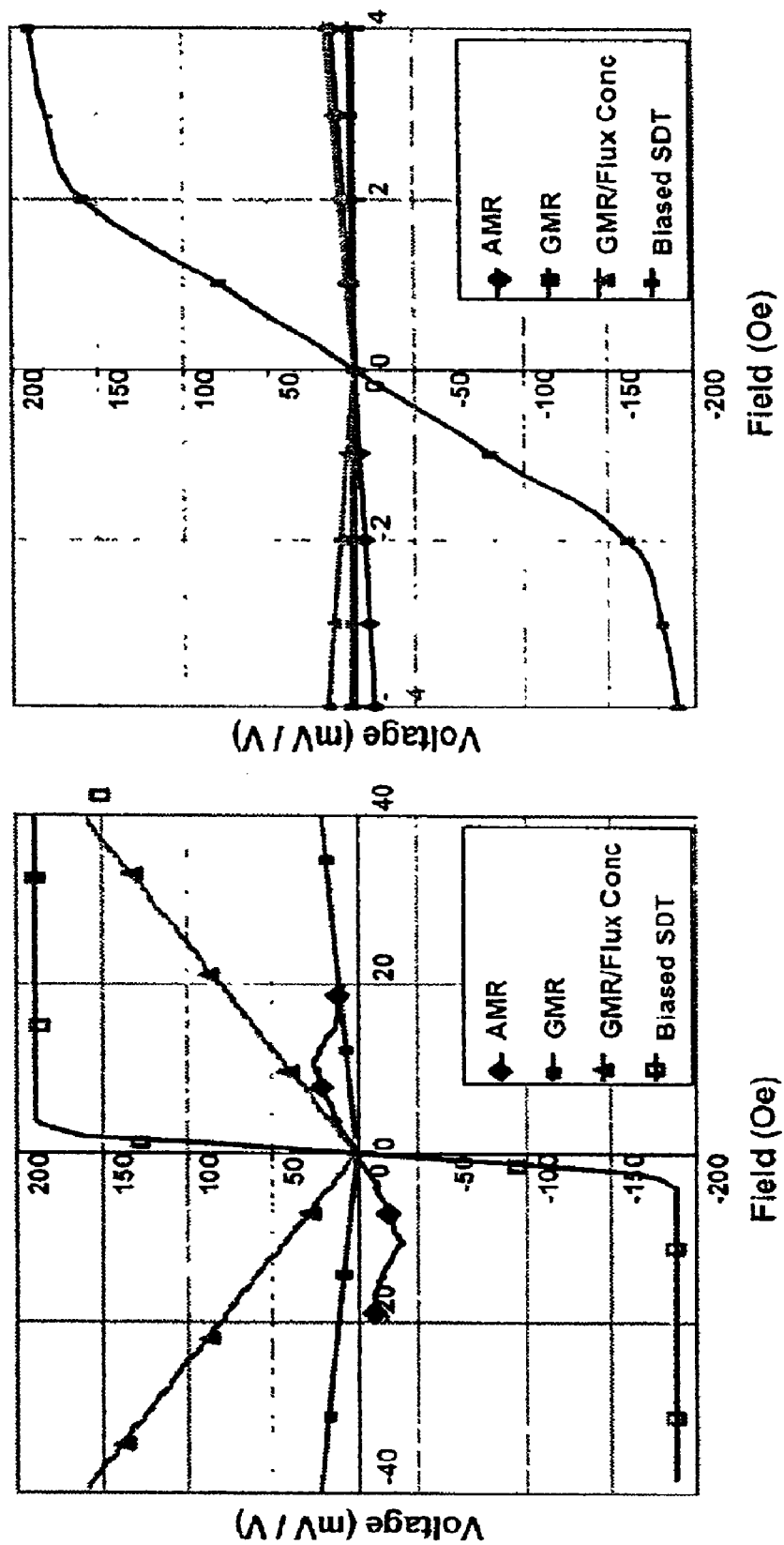

FIG. 28 is a graphical comparison between the outputs for various magnetoresistive sensors including conventional GMR materials with and without flux concentrators. The GMR sensor shows the characteristic unipolar behavior which does not differentiate north from south. The AMR sensor shows its typical behavior of reaching a peak output and then decreasing. Note the significantly larger sensitivity for the bipolar SDT sensor compared to the bipolar AMR sensor and the unipolar GMR sensors.

Figure 29:
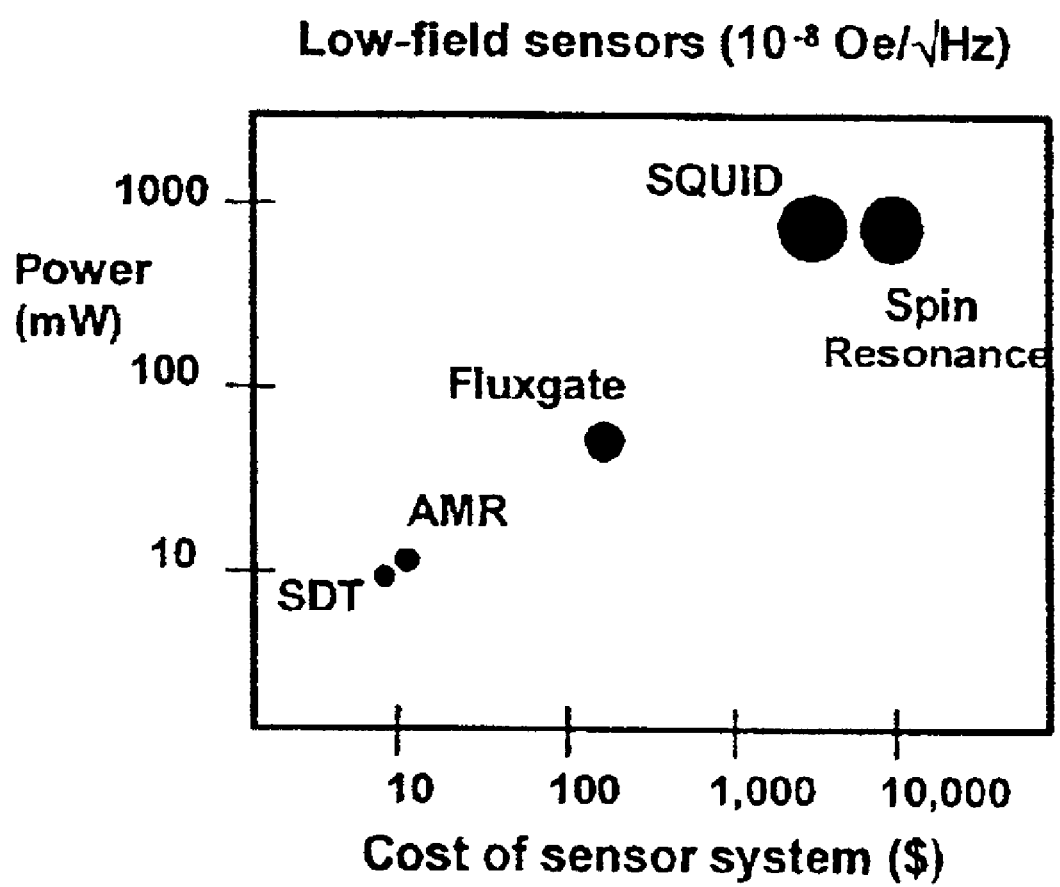

FIG. 29 is a graphical comparison of cost, power and size of several low field sensors. These sensors were all designed with the same minimum field resolution of $10^{-8}$ Oe/$\sqrt{Hz}$, limited by thermal noise. There is a significantly larger sensitivity for the bipolar SDT sensor compared to the bipolar AMR sensor and the unipolar GMR sensors. Newly developed SDT materials present a sensitivity of 8.25%/Oe or an output of over 80 mV/V/Oe, without flux concentrators, and an hysteresis of 0.06 Oe.

Figure 30:
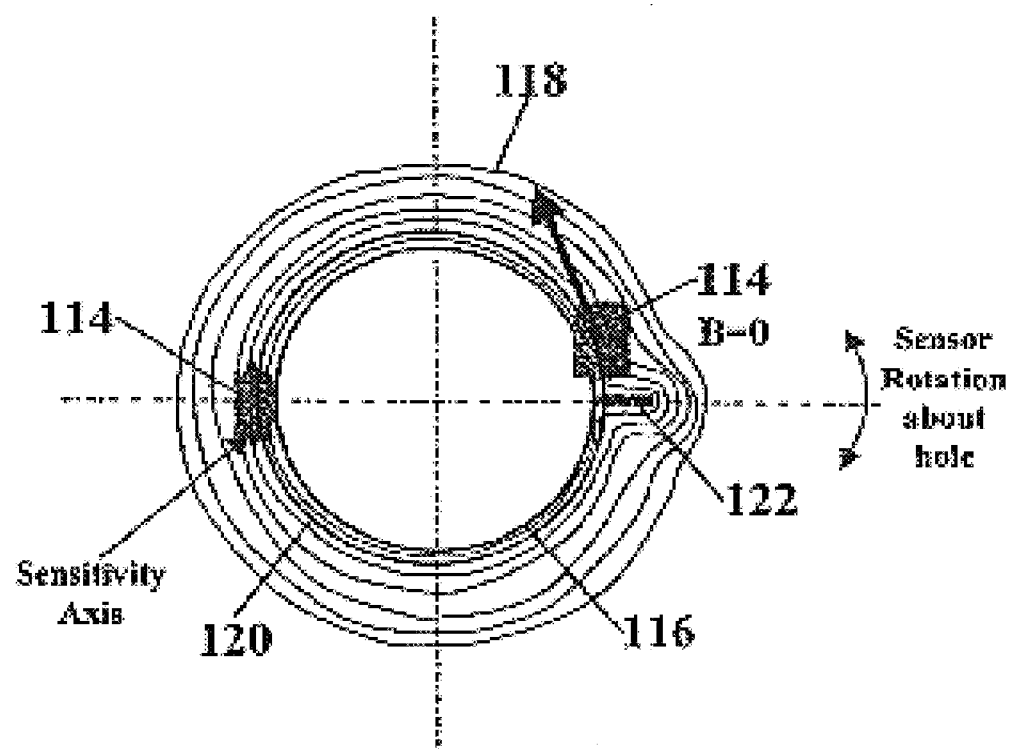
FIG. 30 is a schematic drawing illustrating the principle of operation of an eddy current probe for measuring defects around holes.

FIG. 30 is a schematic drawing illustrating the principle of operation of the eddy current probe (shown as reference numeral 110) in FIGS. 24 and 25. In the absence of defects, the eddy currents 118 produced by the coil (shown as reference numeral 112 in FIGS. 24 and 25) are circular and the maximum current density is obtained under a mean radius 120 of the coil. Therefore, in this case, the magnetic field along the eddy current lines (e.g., the field tangential to a contour of the hole) is zero and produces no output signal at the sensor 114. A crack 122, perpendicular to the edge 116 of the hole, deviates the eddy current flow. The radial component of the deviated eddy currents, as they flow around the crack 122, produce a magnetic field in the circumferential direction. This circumferential field is detected as the sensor 114 passes over the crack 122. Maximum magnitudes are measured when the sensor 114 is on either side of the crack 122. When the sensor 114 is exactly above the crack 122, the field is zero, because the eddy currents flow in opposite directions along the two sides of the crack 122.

Preliminary experiments using the eddy current probe (shown as reference numeral 110 in FIGS. 24 and 25) utilize "tangential" detection. When the sensor 114 is scanned over the region of the crack 122 at different radii extending out from the bole, the maximum detected magnetic field is obtained when the sensor 114 is approximately above the edge 116 of the hole, regardless of the length of the crack 122. This is not the case if the perturbation field, created by the crack 122, is detected either in a radial direction or in a perpendicular direction to a surface of the structure. For methods that detect fields in these directions, the maximum signal is obtained when the sensor 114 is located above a tip of the crack 122. Therefore, for optimum detection, such methods require a radial scan in addition to the circumferential scan.

The configuration of the eddy current probe also helps the electromagnetic field penetrate into the multi-layered structure (shown as reference numeral 108 in FIGS. 24 and 25). When the aluminum multi-layered structure is clamped together using a stainless steel bolt, the stainless steel bolt has a lower electrical conductivity than aluminum. The stainless steel fastener thus acts as a guide for the electromagnetic field and helps the electromagnetic field penetrate deeper into the aluminum structure. Because of the conservation of the electric field at the periphery of the hole, the eddy current intensity around the hole is higher than if the hole is filled with aluminum.

Figure 31:
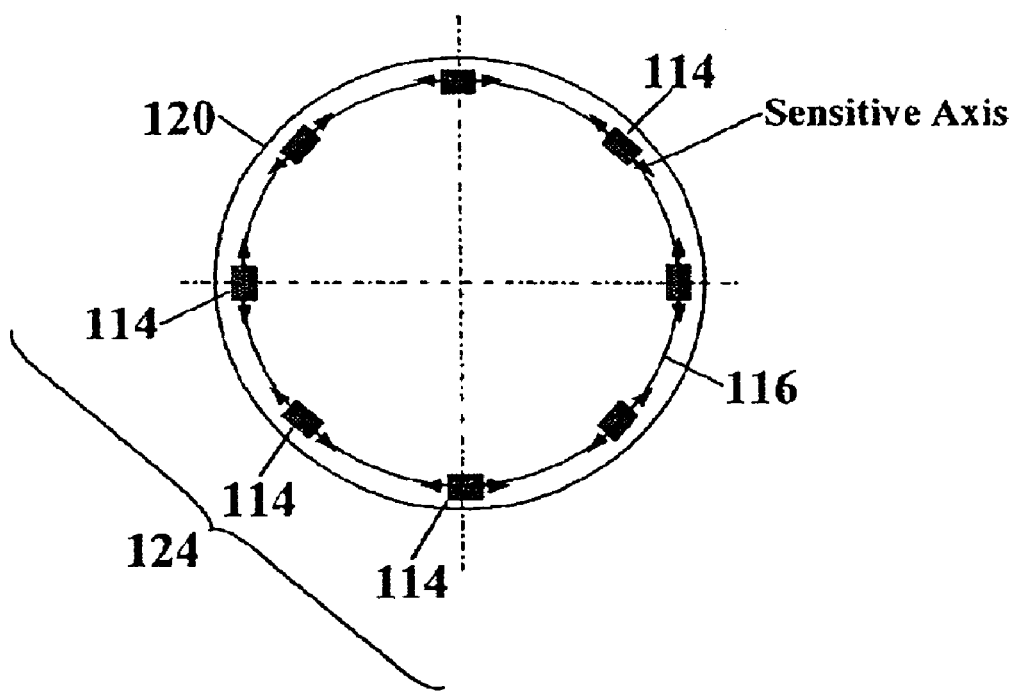
FIG. 31 is a schematic drawing showing the probe including an array of circumferentially-spaced sensors.

FIG. 31 is a schematic drawing showing the probe including an array 124 of eight (8) circumferentially-spaced sensors 114. A complete circumference may be measured by rotating the sensor array 124 an angle of forty five degrees (45° being the angular pitch of the sensors). Those skilled in the art will recognize that adding more sensors could reduce the rotation angle. When the sensors are sufficiently densely packed, rotation becomes unnecessary.

This eddy current probe (shown as reference numeral 110 in FIGS. 24 and 25) has other design considerations. Because the probe's output signal is zero in the absence of defects, the probe is self-nulling. Few, or no, additional compensation techniques are needed to eliminate fields produced by the excitation coil (shown as reference numeral 112 in FIGS. 24 and 25) and by eddy currents induced in the structure (shown as reference numeral 108 in FIGS. 24 and 25). In the absence of defects, the presence of the edge 116 and the fastener does not produce a signal. The maximum sensor output always occurs near the edge 116 of the hole, therefore requiring only one circumferential scan along the edge 116 for optimum detection of cracks of arbitrary length. For lower conductivity bolts the concentric configuration provides deeper penetration of eddy currents around the hole. The array of sensors could be custom manufactured for distribution along the hole circumference to reduce or eliminate mechanical scanning. A concentric coil will result in localized eddy currents around the hole to be inspected, thereby reducing interference from other adjacent holes or edges.

Figure 32A:
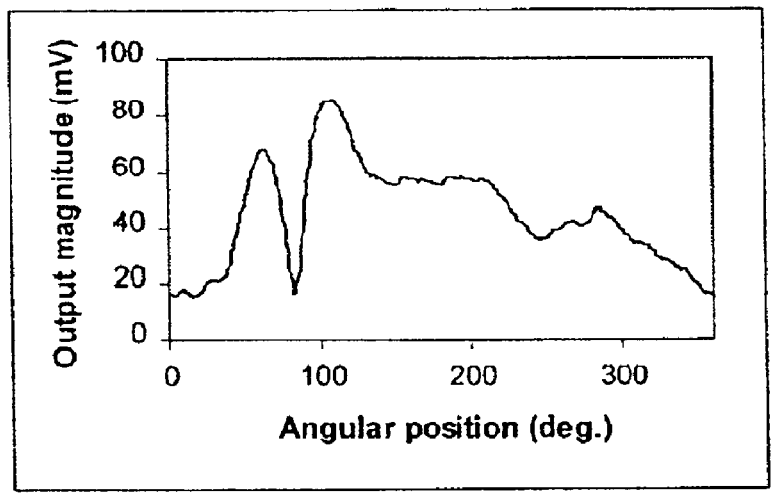
FIGS. 32A and 32B are graphs illustrating preliminary test results using the eddy current probe of FIG. 24.
Figure 32B:
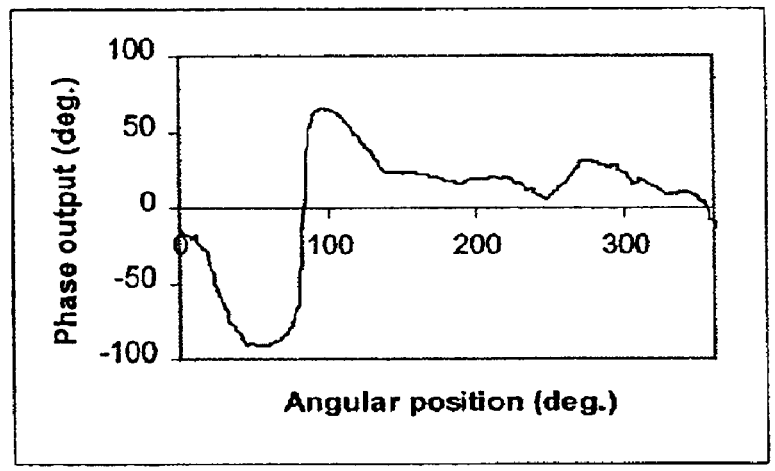

FIGS. 32A and 32B are graphs illustrating preliminary test results using the eddy current probe of FIG. 24. This eddy current probe (shown as reference numeral 110 in FIG. 24) had the sensor placed under the coil winding. The test specimen consisted of a square plate of aluminum of 6.25 mm (0.25 inch) thickness, with a hole of 19 mm (0.75 inch) diameter in the middle of the specimen. Two corner cracks, of 0.15 mm width and extending perpendicular from the hole edge, were machined on one side of the specimen. The cracks were located on opposite sides of the hole (spaced at 180 degrees around the circumference) and have the following dimensions (height and length): 2.5 mm×2.5 mm and 1.25 mm×1.25 mm. In the experimental setup, the eddy current probe was placed near the aluminum plate on the opposite side to the surface containing the cracks. The probe was held in a stationary fixture above the aluminum plate, while the specimen was rotated using a rotary table. A coil of 19 mm mean diameter containing seventy (70) turns of 0.2 mm diameter copper wire was used for this experiment. A sinusoidal current of 1.2 $A_{RMS}$ was supplied to the coil. The signal from the sensor was amplified, and the signal amplitude and phase were extracted using a Stanford SR850 lock-in amplifier. The excitation frequency was varied to obtain the maximum signal from the crack.

FIG. 32A is a graph of the sensor's output magnitude, while FIG. 32B is a graph of the sensor's output phase. Both the amplitude and phase are from a full circular scan of the sensor above the edge of the hole. The location of the cracks can be inferred between the two peaks of the magnitude plot. The location of the cracks may also be inferred from the phase map at the point where the phase slope is maximum in magnitude. Being generally less noisy, the phase plot provides a more reliable signature for detecting the location of the crack. The first crack, of 2.5 mm, can be clearly located from both plots and occurs at approximately eighty degrees (80°) from the starting point. The second crack, of 1.2 mm, is visible on the phase map and can be located at approximately 260°.

Figure 33A:
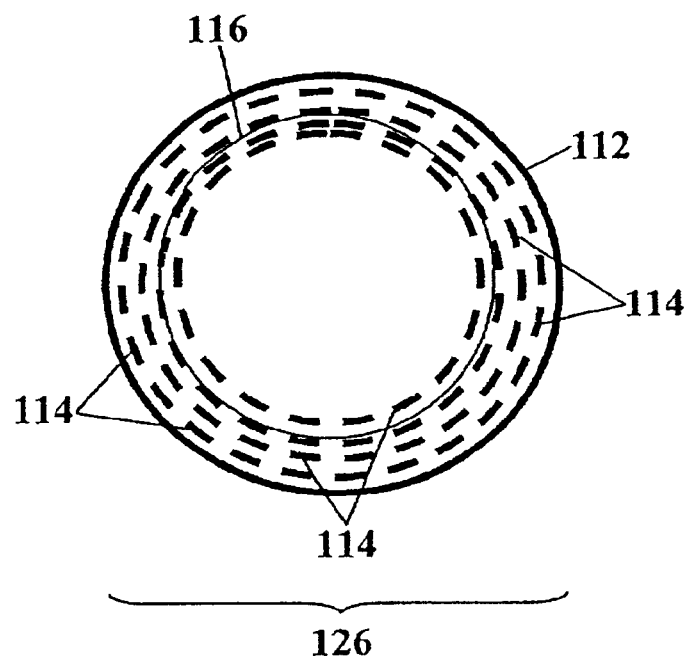
FIGS. 33A and 33B are further examples of an eddy current probe.
Figure 33B:
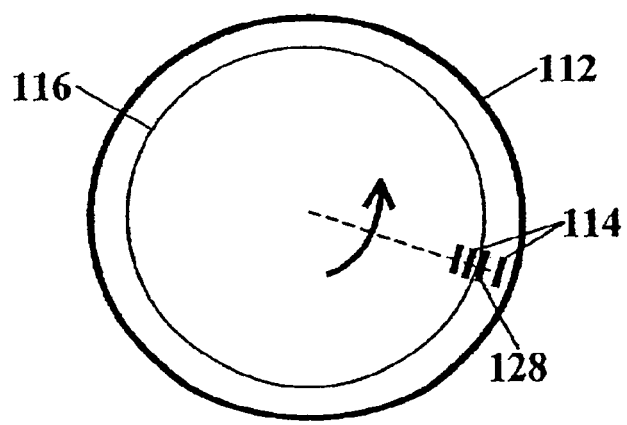

FIGS. 33A and 33B are further examples of an eddy current probe for mapping cracks around a hole. FIG. 33A is a schematic drawing showing the excitation coil 112 and an array 126 of sensors 114. Here the sensors 114 in the array 126 are arranged in both circumferential and radial directions. The sensors 114 in the array 126 are arranged in a ring around the edge 116 of the hole. As FIG. 33A shows, the sensitive axes of the sensors 114 are tangential to the edge 116 of the hole. FIG. 33B is a schematic drawing showing the excitation coil 112 and an array 128 of radially-disposed sensors 114. The array 128 is rotated above the circumference of the edge 116 of the hole. As FIG. 33B demonstrates, only one circular scan is necessary to map a ring containing the region where cracks may be present.

The principles of the present invention may also be applied to shaped eddy current probes. These shaped eddy current probes further help detect cracks around rivet holes. There is, for example, an increased interest in detecting fatigue cracks within assembled structures and, in particular, around fastener holes in aging aircraft. The eddy current probes of the present invention result in an enhanced capability for the measurement of deeply buried flaws initiating from fastener holes. The excitation field is produced by a shaped coil, such as "D"-shaped or a double-"D"-shaped coil, that serves to focus the eddy current density around the hole contour where cracks can initiate.

Figure 34A:
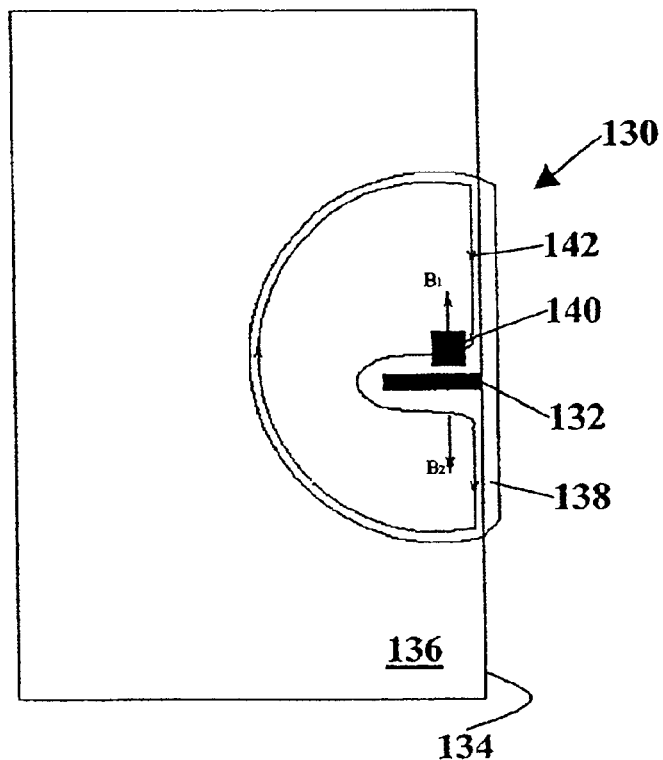
FIGS. 34A and 34B show the operating principle of "D"-shaped excitation coils.
Figure 34B:
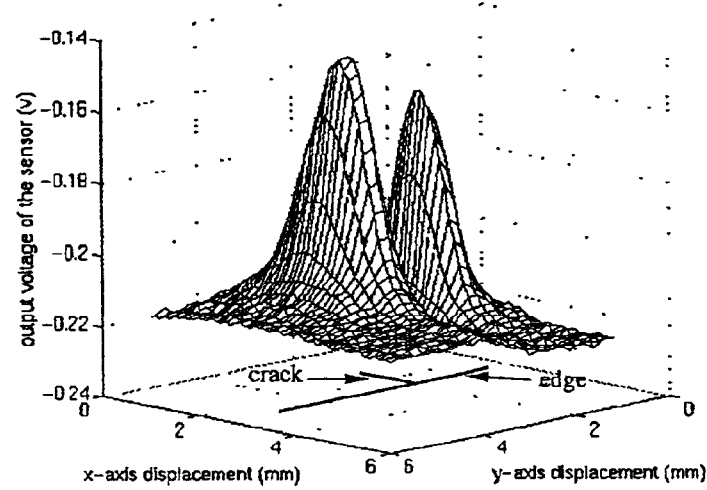

FIGS. 34A and 34B show the operating principle of "D"-shaped excitation coils. FIG. 34A is a schematic drawing of a probe 130 for detecting a crack 132 initiating at a straight edge 134 of a specimen 136. This probe 130 includes a "D"-shaped excitation coil 138 and a sensor 140. If sensitive axis of this probe 130 is properly oriented (parallel to the edge 134 and perpendicular to the crack 132), the edge signal is eliminated. In the absence of the crack 132, the induced eddy currents 142 are constrained to flow along the edge 134 of the specimen 136. In this case the eddy current loops 142 are symmetrical about an axis perpendicular to the edge 134. Under this circumstance there will be no output from the sensor 140. In the presence of the crack 132, the current flow along the edge 134 is perturbed, and the current is forced to flow around the crack 132. The current flow along the sides of the crack 132 creates the components of the magnetic field $B_1$ and $B_2$. When the sensor 140 is exactly above the crack 132, these two components cancel each other and result in zero output. When the sensor 140 is moved so that it is asymmetric above the crack 132, there will be an imbalance between the two field components, thereby producing a signal at the sensor output. FIG. 34B is a graph of the output signal of the probe 130. A two-peak signal is obtained when the probe 130 was scanned across a one millimeter (1 mm) edge crack. The sensitive axis of the sensor 140 is aligned perpendicular to the crack 132 (and, thus, parallel to the edge 134). There will also be a component of the eddy currents that flow underneath (in the case of surface edge crack), above (in the case of bottom edge crack) or both (in the case of interior crack initiating from the edge). Because this flow does not contribute to the signal detected by the sensor 140, however, these eddy current flows are not shown. These currents, on the contrary, diminish the flow around the crack 132, resulting in a decreased output signal, and are often considered as leakage or losses.

Figure 35A:
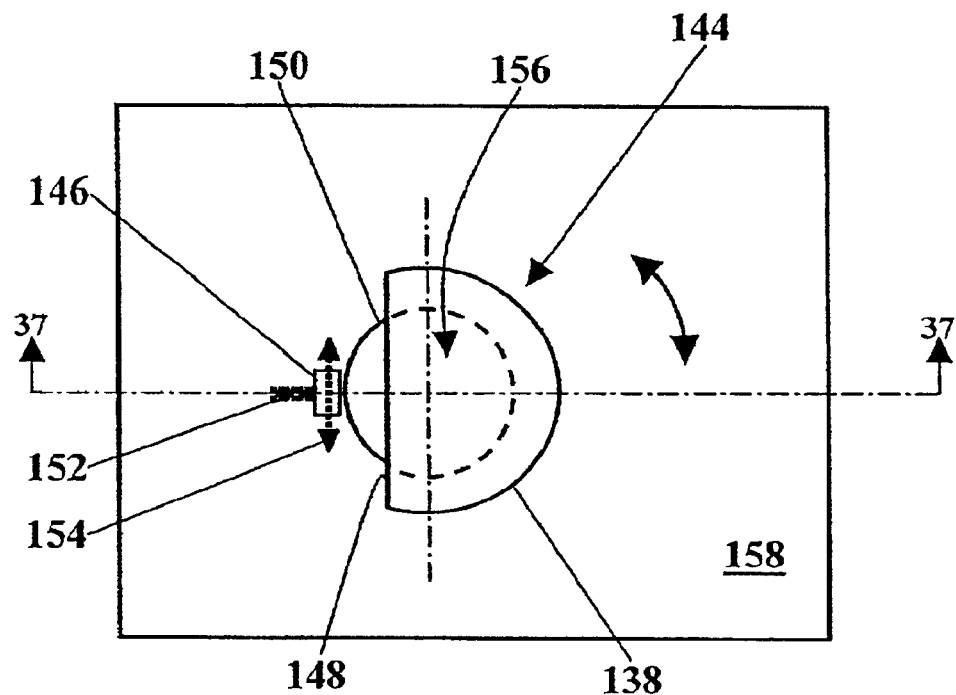
FIGS. 35A and 35B are further examples of "D"-shaped coils.
Figure 35B:
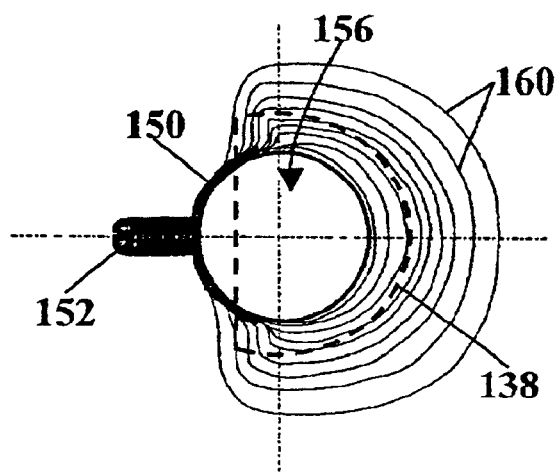

FIGS. 35A and 35B are further examples of "D"-shaped coils. FIG. 35A is a plan view of a "D"-shaped probe 144 with an externally positioned sensor 146. The "D"-shaped coil 138 is placed with its straight edge 148 intersecting a hole region. Using this configuration, most eddy current loops are constrained to follow the path along an edge 150 of a hole where a crack 152 is detected. The sensor 146 is both external to the excitation coil 138 and attached to the excitation coil 138, so both the excitation coil 138 and the sensor 146 simultaneously rotate around the hole. The sensor 146, as shown in previous configurations, is positioned above the edge 150 of the hole, with a sensitive axis 154 tangential to this edge 150. FIG. 35B is a schematic drawing of the eddy current loops 160. Because the eddy current loops flowing in the fastener 156, and also those flowing above/underneath the crack 152, do not contribute to measured signal, these eddy current loops are not represented.

Figure 36A:
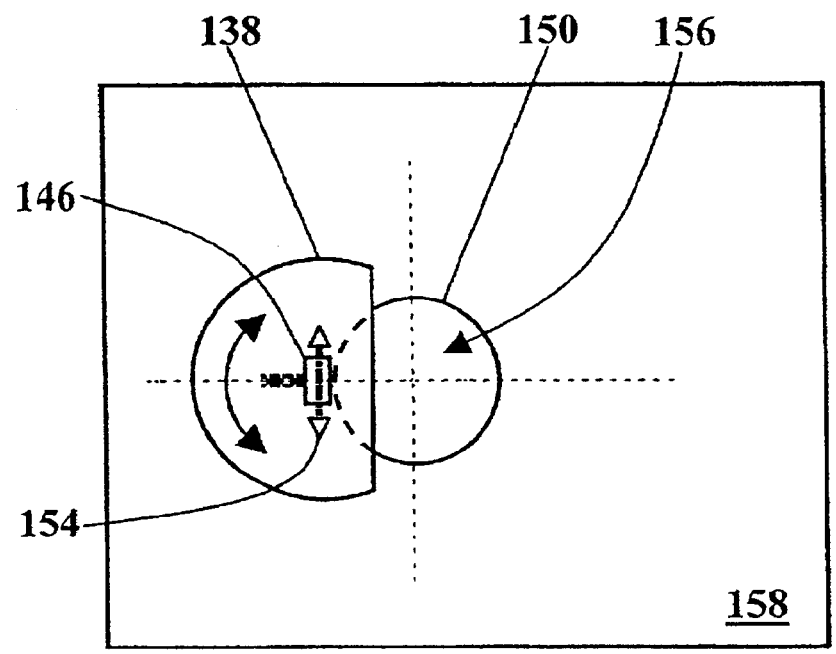
FIGS. 36A and 36B show an alternate probe configuration.
Figure 36B:
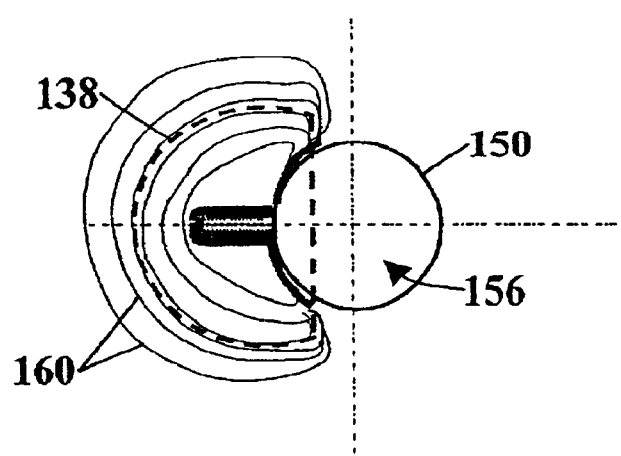

FIGS. 36A and 36B describe an alternate probe configuration. FIG. 36A is a schematic drawing showing the sensor 146 placed interior to the "D"-shaped excitation coil 138 and above the circumference of the hole, again with the sensitive axis 154 tangential to the hole. The probe 144 is rotated around the hole, with the sensor 146 describing a circular path corresponding to the contour of the hole. FIG. 36B shows that the bole acts as a concentrator for the eddy current flow, forcing most of the eddy currents 160 to flow along the edge 150 of the hole and, therefore, flow directly below the region where the sensor 146 is located. This eddy current flow is possible because the maximum density eddy current loops, which correspond to the contour of the coil 138, follow the path of least resistance. Because the interface between the test specimen 158 and the fastener 156 has a significant electrical resistance, the current is deviated from a circular trajectory, being concentrated along the edge corresponding to the location of the sensor 146. The eddy current loops of radius larger than the coil radius will close on the opposite side of the hole. Because these large radius eddy current loops do not flow in the region of interest where the sensor 146 is located, these large radius eddy current loops represent losses. Small eddy current loops, however, will also exist in the fastener. Because these small radius eddy current loops are symmetrical, they will produce no signal at the sensor 146.

Figure 37:
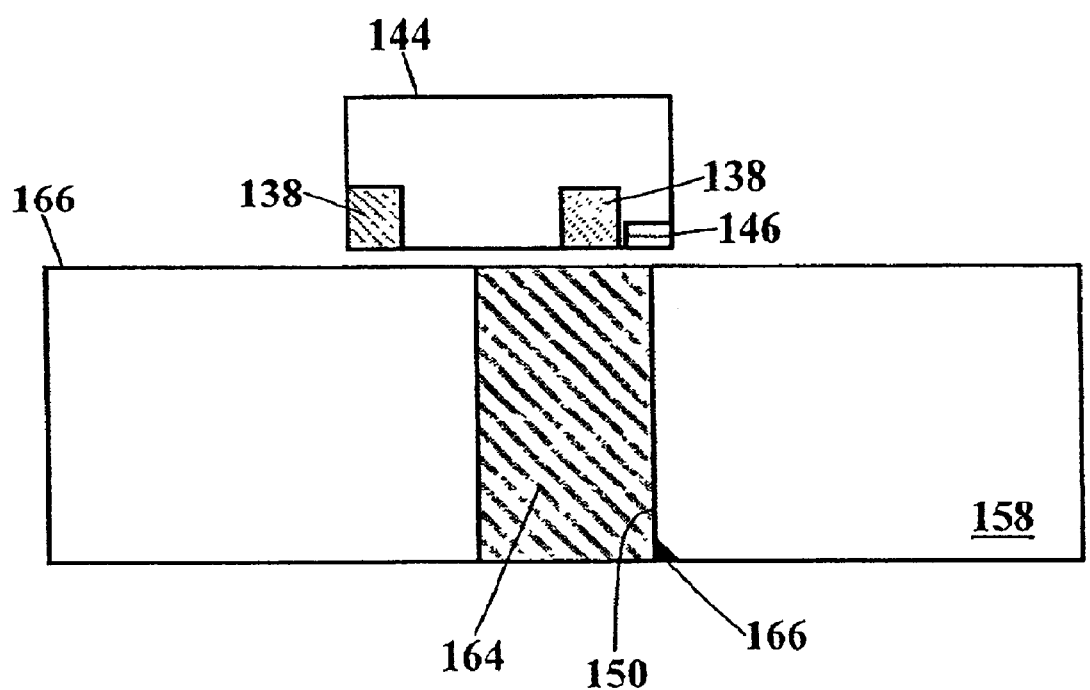
FIG. 37 is a sectional view of the probe and the test specimen taken along line $L_{37\text{-}37}$ of FIG. 35A.

FIG. 37 is a sectional view of the probe 144, and the test specimen 158, taken along line $L_{37\text{-}37}$ of FIG. 35A. The test specimen 158 contains one ten millimeter (10 mm) layer of aluminum. The hole, of nineteen millimeters (19 mm) in diameter, was filled with a stainless steel rod 164 to emulate a fastener. A corner crack 166, of 2.8 mm in length and 2.8 mm in height, was machined on the edge 150 of the hole at a bottom surface of the specimen 158. In the experimental setup, the eddy current probe 144 was placed near a top surface 166 of the aluminum specimen 158, opposite the bottom surface containing the crack 166. The probe 144 was held in a stationary fixture above the aluminum specimen 158, while the specimen 158 was rotated using a rotary table.

Experiments were then conducted to compare circular coils and "D"-shaped coils. Several circular and "D"-shaped coils, all having the same maximum diameter of forty five millimeters (45 mm), were manufactured. The coils contain fifty (50) turns of 0.4 mm diameter copper wire, and each coil was supplied a sinusoidal current of 2.5 A amplitude. The signal from the sensor 146 was amplified (×2), and the amplitude and phase were extracted using a Stanford SR850 lock-in amplifier. The frequency was varied until the maximum signal from the crack 166 was observed.

Figure 38A:
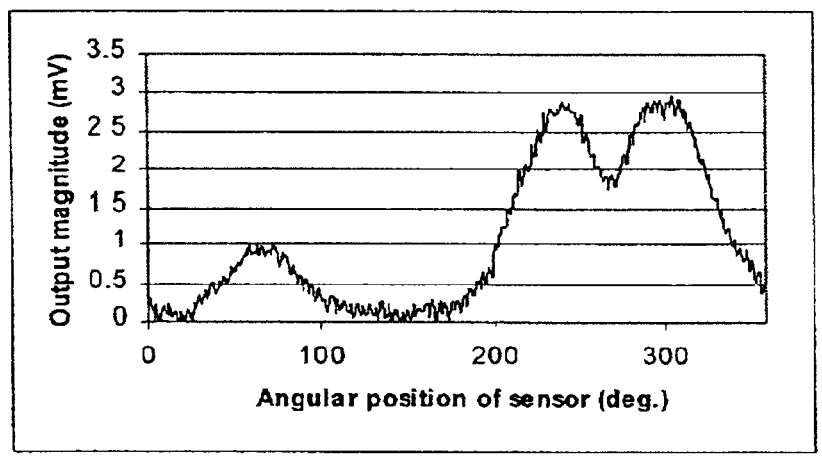
FIGS. 38A and 38B are graphs of the maximum output magnitude and phase obtained from testing.
Figure 38B:
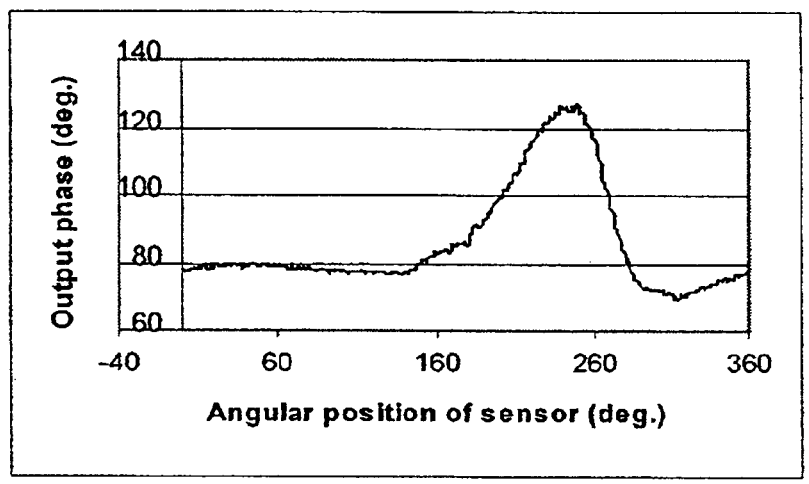

FIGS. 38A and 38B are graphs of the maximum output magnitude and phase obtained from these tests. A circular coil was first concentrically positioned over the hole, however, no signal from the backside crack could be detected after a complete 360° rotation of the probe. Subsequently, an inspection was performed using a "D"-shaped coil with the sensor located externally (as shown and as described with reference to FIG. 35). Both magnitude and phase representations of the output from a circular scan using the "D"-shape coil are shown in FIGS. 38A and 38B. The location of the crack can be inferred from the magnitude plot as occurring at the valley between the two symmetrical peaks, or from the phase map at the point where the phase slope is a maximum in magnitude. From these plots, it can be noticed that the phase map is less noisy, being preferred for detecting the location of the crack. In the future, sensor gradiometers (containing two sensors located at a distance equal to the distance between the two peaks from the magnitude map) can be used. The use of gradiometers will increase the sensitivity of the probe. At the same time, the phase map will present a maximum at the crack location, the single peak maps being preferred for the ease of interpretation.

These preliminary results demonstrate the "D"-shaped probe is superior to traditional configurations. Small corner cracks, of about 2.8 mm at a depth of 10 mm, were successfully detected in aluminum using these probes. Extensive studies on all proposed configurations will be conducted to determine the best design for deep crack detection around fasteners in multi-layers structures. Also, sandwiches of titanium and aluminum containing cracks that simulate real wing structures will be tested. Optimization of coil parameters, driving circuitry, coil and sensor positioning and orientation, sensor noise reduction techniques, and use of more sensitive SDT sensors, are expected to improve the performance of the eddy current probes described herein.

Figure 39:
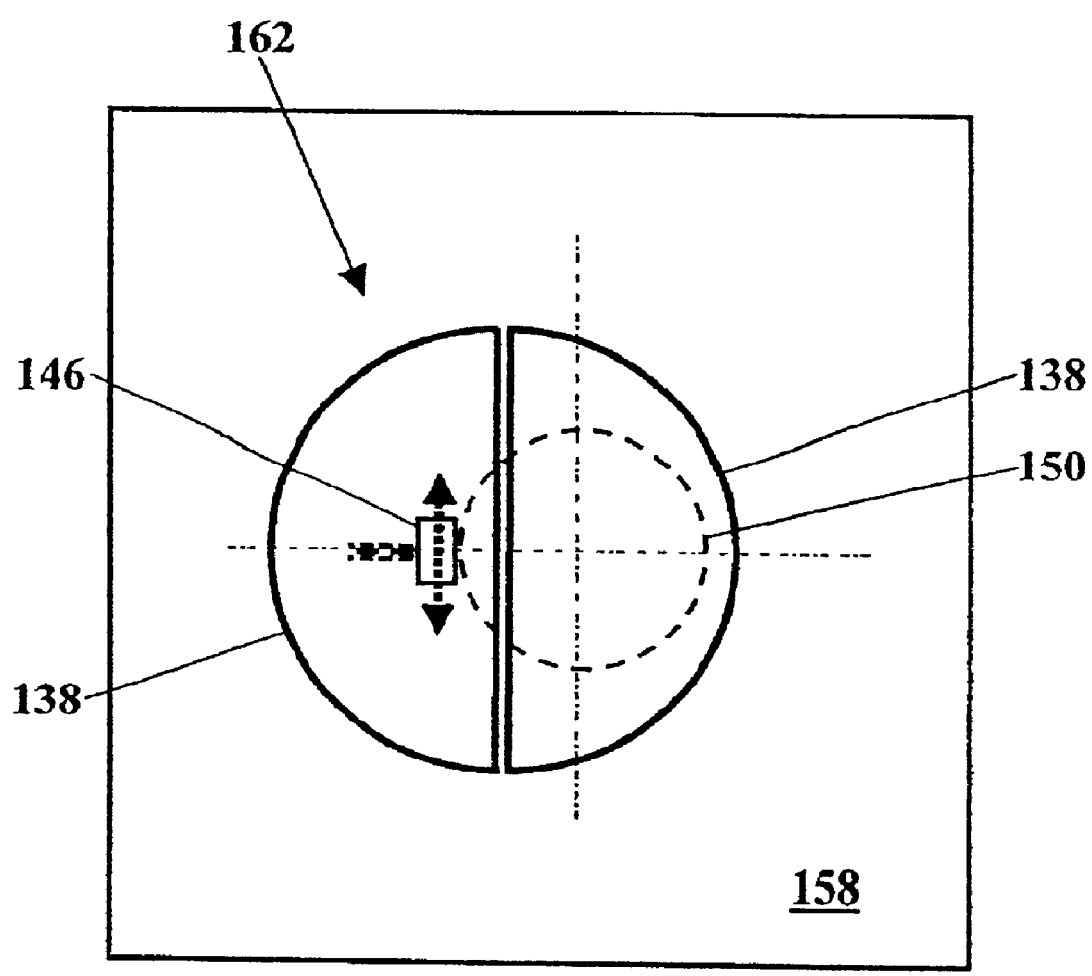
FIG. 39 is a schematic drawing of a double "D"-shaped coil.

FIG. 39 is a schematic drawing of a double "D"-shaped coil 168. The current flow due to both "D"-shaped coils along the straight components of "D" will add to increase the eddy current density.

Figure 40:
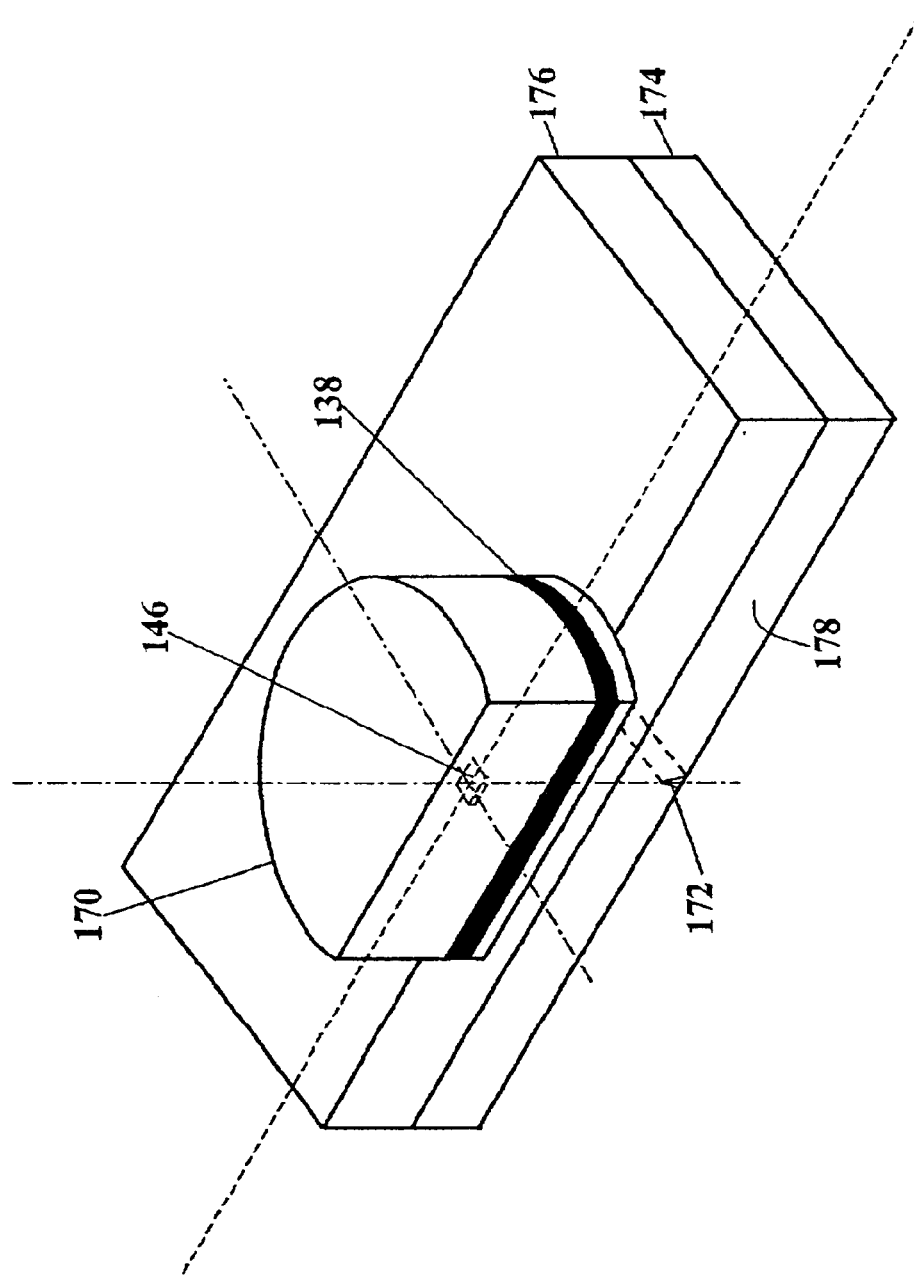
FIGS. 40–42 demonstrate the detection of deeply buried edge cracks in aluminum structures.
Figure 41A:
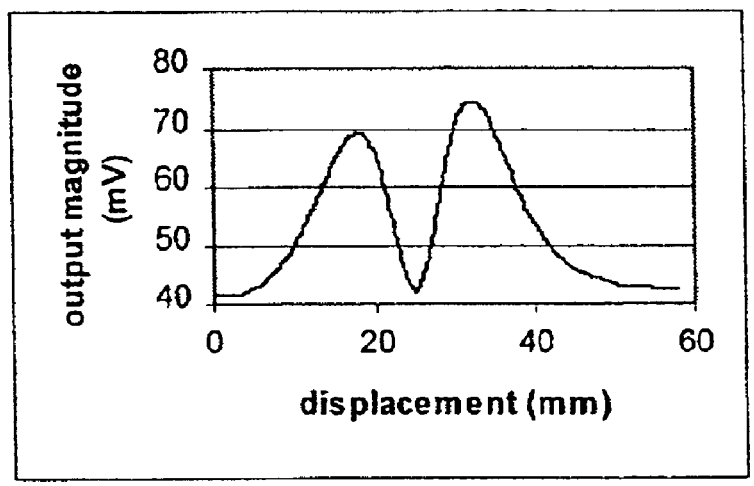
Figure 41B:
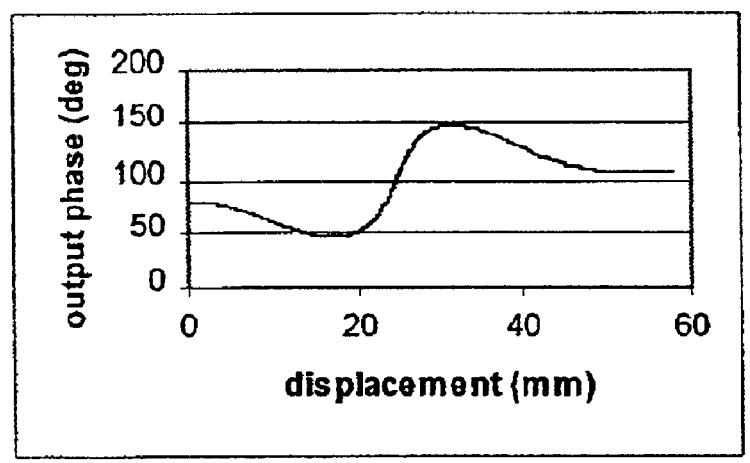
Figure 42A:
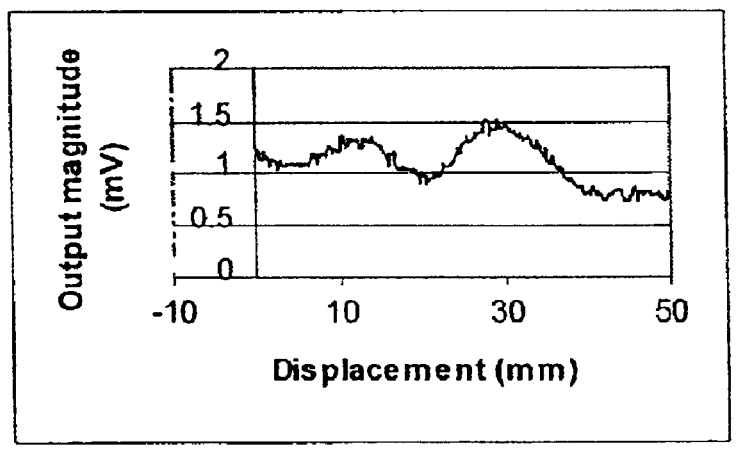
Figure 42B:
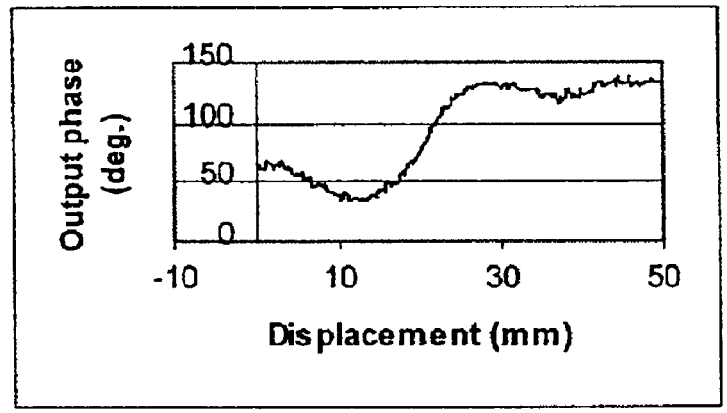

FIGS. 40–42 demonstrate the detection of deeply buried edge cracks in aluminum structures. FIG. 40 is a schematic drawing showing an eddy current probe 170, comprising the "D"-shaped excitation coil 138 and a spin-dependent tunneling (SDT) sensor 146, can detect a short edge slot 172 through a stack of two (2) aluminum plates 174 and 176. The detected slot 172 initiates at an edge 178 and is oriented perpendicular to that edge. Two machined slots were tested: the first had a length of fifteen millimeters (15 mm) and a height of three millimeters (3 mm), while the second slot had both a length and a height of three millimeters (3 mm). The fifteen millimeters slot was detected at a depth of twenty three millimeters (23 mm) below the surface, while the three millimeters (3 mm) slot could still be measured at a depth of 15.5 mm. The true penetration depth, which is smaller than the standard skin depth, is limited by the coil diameter, regardless of the frequency used for the excitation field. Therefore to detect deeper flaws, a larger coil is necessary. As a rule, the mean radius of the coil has to be greater than the depth at which the defect is located to obtain a significant output from the eddy current probe.

The probe geometry minimizes the lift-off for both the coil 138 and the sensor 146 with respect to the plates 174 and 176. To obtain zero output of the sensor 146 in the absence of the slot 172, the sensor 146 has been placed on the symmetry axis of the excitation coil 138. The sensitive axis is oriented parallel to the edge 178 and perpendicular to the slot 172. The excitation coil 138 used in subsequent experiments had a mean diameter of forty five (45 mm), a height of three millimeters (3 mm), and comprised forty (40) turns of 0.58 mm diameter wire. The dimensions of the coil 138 have been chosen such that it enables inspections of flaws at depths of up to about twenty millimeters (20 mm) below the surface regardless of the frequency used.

FIGS. 41 and 42 are graphs showing the output signals. FIG. 41 is a graph of the output signal when first testing the single aluminum plate 174, while FIG. 42 graphs the output signal when using both aluminum plates 174 and 176. The single plate 174 had a thickness of twelve millimeters (12 mm) and contained a surface edge slot 172 of fifteen millimeters (15 mm) in length and three millimeters (3 mm) in depth. The eddy current probe 170 was placed on the opposite top surface of the plate 174, to detect the backside edge of the slot 172. The probe 170 was scanned along the edge 178, with the sensor 146 aligned above the edge 178. An alternating current of 2.4 A amplitude was passed through the excitation coil 138. The frequency was varied until the maximum signal from the slot 172 was obtained. For this plate thickness (12 mm), maximum output signal due to the slot 172 was observed at 200 Hz. The output signal from the SDT sensor 146 was amplified (×2), and its amplitude and phase were extracted using a lock-in amplifier. FIG. 39 shows the output signal when testing both aluminum plates 174 and 176. The same slot 172 was measured, and the edges of each plate were aligned. The additional aluminum plate 176 had a thickness of fourteen millimeters (14 mm). Maximum signal from the slot 172, now buried twenty three (23) mm below the surface, was obtained at a lower frequency of 100 Hz.

The location of the slot 172 can be found at the mid-distance between the two peaks of the magnitude plot, or at the point corresponding to the maximum slope of the phase plot. It can be noticed that the slot signal can still be clearly distinguished from noise in the case of the slot 172 at a depth of twenty three millimeters (23 mm), despite the presence of an interface between the stacked plates 174 and 176.

A short crack of three millimeters (3 mm) in length has also been detected. Here, however, the second aluminum plate 176 only had a thickness of 6.5 mm. This crack, also of three millimeters in 3 mm height, was therefore detected at a depth of 15.5 mm under the surface. An unambiguous signal was observed in both magnitude and phase representations. The results indicate that this method is suitable for deep, short crack detection, where the length of the crack is comparable to its height (typical corner cracks encountered in riveted multi-layers). In addition, from our initial studies, we can conclude that the phase signal is less noisy than the magnitude signal. Based on this observation, it is expected that phase gradiometry (the phase difference between two data points over a defined distance or phase slope) is more suitable to detection and identification of small deeply buried cracks. It is envisaged that ongoing optimization will continue to improve the performance of this probe.

Figure 43:
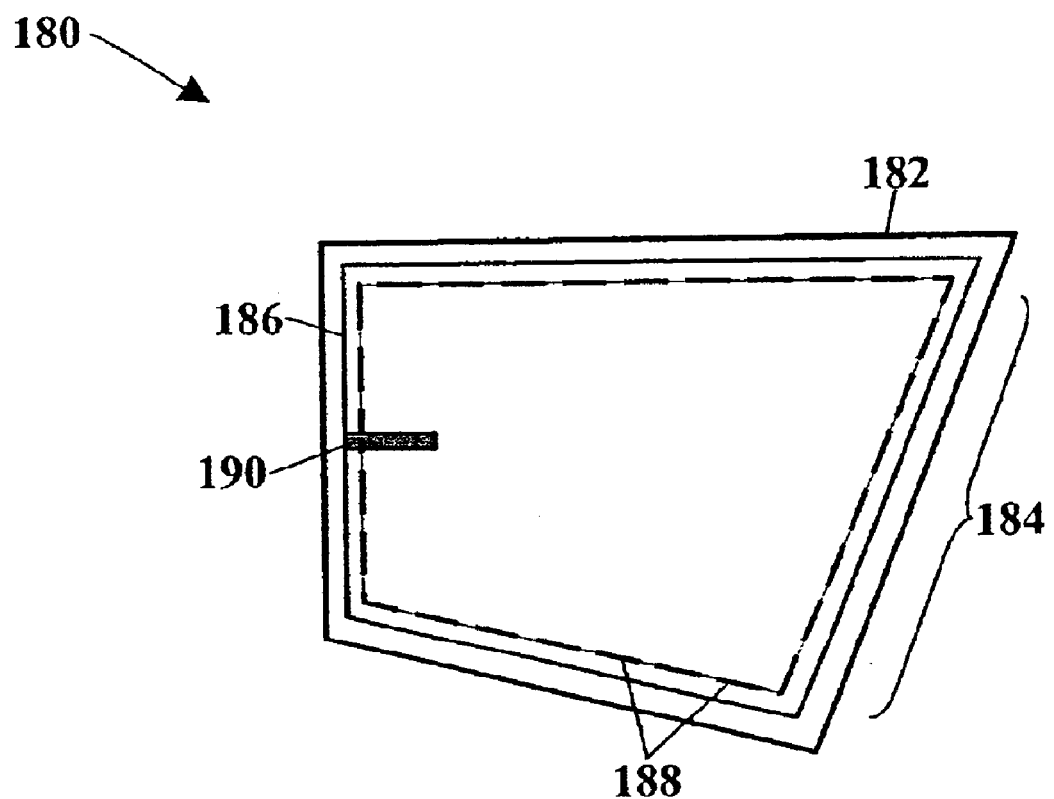
FIG. 43 is a schematic drawing representing an arbitrarily-shaped eddy current probe.

FIG. 43 is a schematic drawing representing an arbitrarily-shaped eddy current probe 180. This arbitrarily-shaped eddy current probe 180 comprises a shaped excitation coil 182 and an array 184 of sensors. The shaped excitation coil 182 could be fabricated to follow or to match the boundary 186 of a similarly-shaped test specimen. The array 184 of sensors would be disposed along the boundary 186 of the test specimen. Each sensor 188 in the array 184 of sensors would have a sensitive axis tangential to the boundary 186. This arbitrarily-shaped eddy current robe 180 could then detect a crack 190 initiating at an edge of the boundary 186.

In designs of eddy current probes using SDT or GMR sensors, the bias coils presented in this invention can also be used as compensation coils to eliminate fields along the sensitive axis due to the excitation coil or due to asymmetries of the specimen geometry.

While the present invention has been described with respect to various features, aspects, and embodiments, the invention is not so limited. Other variations, modifications, and alternative embodiments may be made without departing from the spirit and scope of the present invention.

What is claimed is:

1. A product for detecting flaws in electrically conductive specimens, comprising:
   a coil for inducing an electromagnetic field in a specimen;
   at least two coplanar magneto-resistive sensors, each magneto-resistive sensor having a sensitive axis in the plane and measuring the electromagnetic field along the sensitive axis and a third sensor for measuring the electromagnetic field in a direction perpendicular to the plane.

2. A product according to claim 1, wherein the at least two coplanar magneto-resistive sensors and the coil are formed on the same substrate.

3. A product for detecting flaws in electrically conductive specimens, comprising:
   a coil for inducing an electromagnetic field in a specimen;
   at least two coplanar magneto-resistive sensors, each magneto-resistive sensor having a sensitive axis in the plane and measuring the electromagnetic field along the sensitive axis and a third sensor for measuring the electromagnetic field in a direction perpendicular to the plane, and wherein the at least two coplanar magneto-resistive sensors, the third sensor, and the coil are formed on a substrate.

4. A product for detecting flaws in electrically conductive specimens, comprising:
   a coil for inducing an electromagnetic field in a specimen; and
   at least two coplanar magneto-resistive sensors, each magneto-resistive sensor having a sensitive axis in the plane and measuring the electromagnetic field along the sensitive axis, wherein the at least two coplanar magneto-resistive sensors comprise giant magneto-resistive sensors orthogonally arranged about a central point and arranged external to the coil, with the coil also having an axis of symmetry about the central point, the axis of symmetry of the coil being orthogonal to the plane of the sensors.

5. A product for detecting flaws in electrically conductive specimens, comprising:
   a coil for inducing an electromagnetic field in a specimen; and
   at least two coplanar magneto-resistive sensors, each magneto-resistive sensor having a sensitive axis in the plane and measuring the electromagnetic field along the sensitive axis, wherein the at least two coplanar magneto-resistive sensors comprise giant magneto-resistive sensors orthogonally arranged about a central point, the coil also having an axis of symmetry about the central point, the axis of symmetry of the coil being orthogonal to the plane of the sensors, with the giant magneto-resistive sensors and the coil formed on a substrate.

6. A product for detecting flaws in electrically conductive specimens, comprising:
   a coil for inducing an electromagnetic field in a specimen; and
   at least two coplanar magneto-resistive sensors, each magneto-resistive sensor having a sensitive axis in the plane and measuring the electromagnetic field along the sensitive axis, and a Hall effect sensor for measuring the electromagnetic field in a direction perpendicular to the plane, wherein the at least two coplanar magneto-resistive sensors comprise giant magneto-resistive sensors orthogonally arranged about a central point, with the coil also having an axis of symmetry about the central point, the axis of symmetry of the coil being orthogonal to the plane of the sensors.

7. A product for detecting flaws in specimens, comprising:
   a plurality of devices, each device comprising at least one coil and at least one two-dimensional magneto-resistive sensor, the at least one coil for inducing an electromagnetic field in a specimen, the at least one two-dimensional magneto-resistive sensor comprising a first magneto-resistive sensor and a second coplanar magneto-resistive sensor, the first magneto-resistive sensor and the second magneto-resistive sensor each having a sensitive axis in the plane and measuring the electromagnetic field along the sensitive axis,
   wherein a flaw creates a perturbation in the induced electromagnetic field, and the at least one two-dimensional magneto-resistive sensor detects this perturbation.

8. A product according to claim 7, wherein each device further comprises a third sensor measuring the electromagnetic field in a direction perpendicular to the plane.

9. A product according to claim 7, wherein the plurality of devices are arranged in a one-dimensional array.

10. A product according to claim 7, wherein the plurality of devices are formed on a substrate.

11. A product according to claim 7, wherein the plurality of devices are arranged in a two-dimensional array.

12. A product according to claim 11, wherein the plurality of devices are formed on a substrate.

13. A product according to claim 11, wherein the at least one two-dimensional magneto-resistive sensor comprises giant magneto-resistive sensors orthogonally arranged about a central point, with the at least one coil having an axis of symmetry about the central point, the axis of symmetry of the coil being orthogonal to the plane of the sensors.

14. A product according to claim 11, wherein the at least one two-dimensional magneto-resistive sensor and the coil are formed on a substrate.

15. A product according to claim 11, wherein each device further comprises a Hall effect sensor measuring the electromagnetic field in a direction perpendicular to the plane, with the at least one two-dimensional magneto-resistive sensor, the Hall effect sensor, and the coil formed on a substrate.

16. A product according to claim 7, wherein the plurality of devices are arranged in a three-dimensional array, the three-dimensional array comprising a stack of two-dimensional arrays, each two dimensional array comprising at least one device formed on a substrate.

17. A product according to claim 16, wherein the at least one two-dimensional magneto-resistive sensor comprises giant magneto-resistive sensors orthogonally arranged about a central point, with the at least one coil also having an axis of symmetry about the central point, the axis of symmetry of the coil being orthogonal to the plane of the sensors.

18. A probe for detecting a flaw, such as a crack, at an edge of an electrically conductive specimen of a specific shape, comprising:

an excitation coil similarly shaped to the specimen for inducing eddy currents in the specimen; and at least one magneto-resistive sensor located above the edge of the specimen, the at least one magneto-resistive sensor having a sensitive axis tangentially-aligned with the edge of the specimen, wherein the flaw at the edge creates a perturbation in the induced eddy currents, and the at least one magneto-resistive sensor detects this perturbation.

19. A probe according to claim 18, wherein the magneto-resistive sensor comprises giant magneto-resistive sensors.

20. A probe according to claim 18, wherein the magneto-resistive sensor comprises spin dependent tunneling sensors.

21. A probe according to claim 18, further comprising an array of magneto-resistive sensors, each magneto-resistive sensor in the array having a sensitive axis tangentially-aligned with the edge of the specimen.

22. A probe according to claim 21, wherein each magneto-resistive sensor in the array comprises giant magneto-resistive sensors.

23. A probe according to claim 21, wherein each magneto-resistive sensor in the array comprises spin dependent tunneling sensors.

24. A probe according to claim 21, wherein the array of magneto-resistive sensors has a circular shape.

25. A probe according to claim 21, wherein the array of magneto-resistive sensors is formed on a substrate.

26. A probe according to claim 18, wherein the excitation coil has a circular shape.

27. A probe according to claim 18, further comprising means for biasing the magneto-resistive sensor to compensate for the earth's magnetic field.

28. An eddy current probe for detecting a flaw in an electrically conductive specimen, comprising:

a coil for inducing eddy currents in the specimen, the coil having a cross-section and an axis of symmetry within a plane of the cross-section; and a magneto-resistive sensor having an axis of sensitivity coplanar with the cross-section and orthogonal to the axis of symmetry, with the magneto-resistive sensor disposed on the axis of symmetry and at least one of i) exterior to the coil and ii) interior to the coil, wherein the flaw creates a perturbation in the induced eddy currents, and the magneto-resistive sensor detects this perturbation.

29. An eddy current probe according to claim 28, wherein the magneto-resistive sensor comprises a giant magneto-resistive sensor.

30. An eddy current probe according to claim 28, wherein the magneto-resistive sensor comprises a spin dependent tunneling sensor.

31. An eddy current probe for detecting a flaw in an electrically conductive specimen, comprising:

a coil for inducing eddy currents in the specimen, the coil having a cross-section and an axis of symmetry within the plane of the cross-section; and an array of magneto-resistive sensors, with each magneto-resistive sensor having an axis of sensitivity coplanar with the cross-section and orthogonal to the axis of symmetry, the array of magneto-resistive sensors disposed on the axis of symmetry and at least one of i) exterior to the coil and ii) interior to the coil, wherein the flaw creates a perturbation in the induced eddy currents, and the magneto-resistive sensor detects this perturbation.

32. An eddy current probe according to claim 31, wherein the array of magneto-resistive sensors comprises a giant magneto-resistive sensor.

33. An eddy current probe according to claim 31, wherein the array of magneto-resistive sensors comprises a spin dependent tunneling sensor.

34. An eddy current probe according to claim 31, wherein the array of magneto-resistive sensors is formed on a substrate.

35. An eddy current probe according to claim 31, wherein the cross-section of the coil has a "D" shape.

36. An eddy current probe according to claim 31, wherein the cross-section of the coil has a double "D" shape.

* * * * *